(12) United States Patent
Chen et al.

(10) Patent No.: US 11,137,394 B2
(45) Date of Patent: Oct. 5, 2021

(54) SYSTEMS AND METHODS FOR PERFORMING IMMUNOASSAYS

(71) Applicant: THE REGENTS OF THE UNIVERSITY OF MICHIGAN, Ann Arbor, MI (US)

(72) Inventors: Pengyu Chen, Ann Arbor, MI (US); Katsuo Kurabayashi, Ann Arbor, MI (US); Timothy T. Cornell, Ann Arbor, MI (US); Thomas P. Shanley, Ann Arbor, MI (US); Meng Ting Chung, Ann Arbor, MI (US); Yujing Song, Ann Arbor, MI (US); Walker M. McHugh, Dexter, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 834 days.

(21) Appl. No.: 15/551,164

(22) PCT Filed: Feb. 16, 2016

(86) PCT No.: PCT/US2016/018060
§ 371 (c)(1),
(2) Date: Aug. 15, 2017

(87) PCT Pub. No.: WO2016/133899
PCT Pub. Date: Aug. 25, 2016

(65) Prior Publication Data
US 2018/0031549 A1    Feb. 1, 2018

Related U.S. Application Data

(60) Provisional application No. 62/245,066, filed on Oct. 22, 2015, provisional application No. 62/116,741, filed on Feb. 16, 2015.

(51) Int. Cl.
*G01N 33/553* (2006.01)
*G01N 33/543* (2006.01)
(Continued)

(52) U.S. Cl.
CPC ...... *G01N 33/54373* (2013.01); *B01L 3/5027* (2013.01); *C40B 40/10* (2013.01);
(Continued)

(58) Field of Classification Search
CPC .......... G01N 21/554; G01N 33/54373; G01N 33/54346; B01L 3/5027; B01L 2400/0457;
(Continued)

(56) References Cited

U.S. PATENT DOCUMENTS

2010/0167958 A1* 7/2010 Lin .................. C07K 1/26
506/30
2012/0164717 A1  6/2012 Irudayaraj et al.
(Continued)

OTHER PUBLICATIONS

Oh et al, "Localized Surface Plasmon Resonance (LSPR) Optofluidic Biosensor For Label-Free Cellular Immunophenotyping", 17th International Conference on Miniaturized Systems for Chemistry and Life Sciences, Oct. 27-31, 2013, Freiburg, Germany.*
(Continued)

*Primary Examiner* — Christopher L Chin
(74) *Attorney, Agent, or Firm* — Casimir Jones, S.C.; Tanya A. Arenson

(57) ABSTRACT

Provided herein are systems and methods for assays. In particular, provided herein are systems and methods for performing high throughput immunoassays. Embodiments of the present disclosure provide multiplex capable LSPR immunoassays that meet a need for rapid (e.g., near real time), accurate immunoassays (e.g. for use in beside diagnostics). The LSPR assays are as accurate as existing ELISA
(Continued)

assays but provide the advantage of increased speed and multiplex capability. In addition, the LSPR immunoassays are able to analyze small volumes of complex patient samples (e.g., serum).

11 Claims, 22 Drawing Sheets

(51) Int. Cl.
  B01L 3/00 (2006.01)
  C40B 40/10 (2006.01)
(52) U.S. Cl.
  CPC ............................ *G01N 33/54346* (2013.01); *B01L 2300/0636* (2013.01); *B01L 2300/0645* (2013.01); *B01L 2300/0816* (2013.01); *B01L 2300/0861* (2013.01); *B01L 2300/0877* (2013.01); *B01L 2300/123* (2013.01); *B01L 2300/161* (2013.01); *B01L 2400/043* (2013.01); *B01L 2400/0406* (2013.01); *B01L 2400/0415* (2013.01); *B01L 2400/0442* (2013.01); *B01L 2400/0457* (2013.01); *B01L 2400/0487* (2013.01)
(58) Field of Classification Search
  CPC ....... B01L 2300/0645; B01L 2400/043; B01L 2300/0816; B01L 2400/0442; B01L 2300/123; B01L 2400/0406; B01L 2400/0415; B01L 2300/0861; B01L 2300/161; B01L 2300/0636; B01L 2300/0877; B01L 2400/0487; C40B 40/10
  USPC ........... 422/82.11, 502, 503, 504; 435/288.7; 436/524, 525, 805
  See application file for complete search history.

(56) References Cited

U.S. PATENT DOCUMENTS

2013/0065777 A1  3/2013  Altug et al.
2014/0271366 A1  9/2014  Denomme et al.

OTHER PUBLICATIONS

Chamanzar et al, "Hybrid integrate plasmonic-photonic waveguies for on-chip localized surface plasmon resonance (LSPR) sensing and spectroscopy", Optics Express, vol. 21, No. 26, Dec. 2013.*
Acimovic, S. S., et al. "LSPR chip for parallel, rapid, and sensitive detection of cancer markers in serum." Nano Lett. 14, 2636-2641 (2014).
Agus, M. S. D., et al. "Tight glycemic control versus standard care after pediatric cardiac surgery." N. Engl. J. Med. 367, 1208-19 (2012).
Ashraf, et al., "Effects of cardiopulmonary bypass on neonatal and paediatric inflammatory profiles" Eur. J. Pediatr. Surg. 12, 862-868 (1997).
Bozza, F. A., et al. "Cytokine profiles as markers of disease severity in sepsis: a multiplex analysis" Critical Care 11, article R49 (2007).
Cant, NE, et al. "Surface functionalisation for the self-assembly of nanoparticle/polymer multilayer films" Thin Solid Films 2003; 426: 31-39.
Chen et al. "Multiplex Serum Cytokine Immunoassays Using Nanoplasmonic Biosensor Microarrays" ACS Nano, Mar. 23, 2015, vol. 9, No. 4, pp. 4173-4181.
Damas, P., et al. "Sepsis and serum cytokine concentrations." Crit. Care Med. 25, 405-412 (1997).
Eck, W. et al. "PEGylated gold nanoparticles conjugated to monoclonal F19 antibodies as targeted labeling agents for human pancreatic carcinoma tissue." ACS Nano 2, 2263-2272 (2008).
Endo, T., et al. "Multiple label-free detection of antigen-antibody reaction using localized surface plasmon resonance-based core-shell structured nanoparticle layer nanochip." Anal. Chem. 78, 6465-6475 (2006).
Erickson et al., "Size and shape of protein molecules at the nanometer level determined by sedimentation, gel filtration, and electron microscopy." Biol. Proced. Online. 15, 32-51 (2009).
Grabarek, Z. & Gergely, "Zero-length crosslinking procedure with the use of active esters." J. Anal. Biochem. 185, 131-135 (1990).
Haddada MB, et al. "Optimizing the immobilization of gold nanoparticles on functionalized silicon surfaces: amine- vs thiol-terminated silane" Gold Bull 2013; 46: 335-341.
International Search Report, International Patent Application No. PCT/US2016/018060, dated Apr. 29, 2016.
Kabashin, A. V. et al. "Plasmonic nanorod metamaterials for biosensing" Nature Mater. 8, 867-871 (2009).
Mayer et. al., "A label-free immunoassay based upon localized surface plasmon resonance of gold nanorods." ACS Nano, 2, 687-692, 2008.
Lippitz, B. E. "Cytokine patterns in patients with cancer: a systematic review" Lancet Oncol. 14, E218-E228 (2013).
Maczynska, I., et al. "Proinflammatory cytokine (IL-1beta, IL-6, IL-12, IL-18 and TNF-alpha) levels in sera of patients with subacute cutaneous lupus erythematosus (SCLE)." Immunot Lett. 102, 79-82 (2006).
Mahle, W. T., et al. "Inflammatory response after neonatal cardiac surgery and its relationship to clinical outcomes." Ann. Thorac. Surg. 97, 950-6 (2014).
Bhagawati et. al. "Quantitative Real-Time Imaging of Protein-Protein Interactions by LSPR Detection with Micropatterned Gold Nanoparticles" Anal. Chem., 85, 9564-9571, 2013.
Melvin et al. "On-chip collection of particles and cells by AC eletroosmotic pumping and dielectrophoresis using asymmetric microelectrodes" Biomicrofluidics, Aug. 10, 2011, vol. 5, No. 3, pp. 1-17.
Nusz et al., "Rational selection of gold nanorod geometry for label-free plasmonic biosensors." ACS Nano 3, 795-806 (2009).
Oh et al. "Localized Surface Plasmon Resonance (LSPR) Optofluidic Biosensor for Label-Free Cellular Immunophenotyping" 17th International Conference of Miniaturized Systems for Chemistry and Life Sciences, Germany, Oct. 31, 2013, pp. 1-3.
Oh, B. et al. "Integrated nanoplasmonic sensing for cellular functional immunoanalysis using human blood." ACS Nano 8, 2667-2676 (2014).
Opal, S. M. & DePalo, "Anti-inflammatory cytokines." V. A. Chest 117, 1162-1172 (2000).
Rosman et.al. "Multiplexed Plasmon Sensor for Rapid Label-Free Analyte Detection" Nano Lett. 13, 3243-3247, 2013.
Rothenberg, E. V. "Cell lineage regulators in B and T cell development" Nat. Immunol. 8, 441-444 (2007).
Seghaye, M. C., et al. "Interleukin-10 Release Related to Cardiopulmonary Bypass in Infants Undergoing Cardiac Operations" J. Thorac. Cardiovasc. Surg. 111, 545-553 (1996).
Visentainer, J. E. L., et al. "Serum cytokine levels and acute graft-versus-host disease after HLA-identical hematopoietic stem cell transplantation." Exp. Hematol. 31, 1044-1050 (2003).
Williams SE, et al. "Controlling the nanoscale patterning of AuNPs on silicon surfaces." Nanomaterials 2013; 3: 192-203.
Wong, H. R., et al. "The pediatric sepsis biomarker risk model" Critical Care 16, article R174 (2011).
Acimovic, S. S., et al. "Supporting Information LSPR Chip for parallel, rapid and sensitive detection of cancer markers in serum" Nanoletters, vol. 14, Apr. 14, 2014, pp. 1-14.
EP Search Report, EP Patent Application No. 16752901.5, dated Jun. 13, 2018, 10 pages.
Han, K.N. et al. "Microfluidic Chips for Immunoassays" Annual Review of Analytical Chemistry, vol. 6, No. 1, Jun. 12, 2013, pp. 119-141.
Mayer et al. "Localized Surface Plasmon Resonance Sensors" Chemical Reviews, vol. 11, No. 6, Jun. 8, 2011, pp. 3828-3857.

* cited by examiner

- Calculation of Limit of Detection (LOD):
  $\sigma_{water} = 0.001176$
  LOD = 36.3 fg/ml (with ACEO)
  LOD = 29.4 pg/ml (without ACEO)

SYSTEMS AND METHODS FOR PERFORMING IMMUNOASSAYS

The present Application claims priority to U.S. Provisional Patent Application Ser. No. 62/116,741 filed Feb. 16, 2015, and U.S. Provisional Patent Application Ser. No. 62/245,066 filed Oct. 22, 2015, each of which is hereby incorporated by reference in its entirety.

STATEMENT REGARDING FEDERALLY SPONSORED RESEARCH OR DEVELOPMENT

This invention was made with government support under 1263889 awarded by the National Science Foundation and under HL119542 awarded by the National Institutes of Health. The government has certain rights in the invention.

FIELD OF THE DISCLOSURE

Provided herein are systems and methods for performing assays. In particular, provided herein are systems and methods for performing high throughput immunoassays.

BACKGROUND

Cytokines are bioactive proteins responsible for cell signaling and regulating the maturation, growth, and responsiveness of immune cells (Opal, S. M. & DePalo, V. A. Chest 117, 1162-1172 (2000); Rothenberg, E. V. Nat. Immunol. 8, 441-444 (2007)). Quantifying cytokines in human serum provides highly valuable clinical information to monitor the immune status of hosts and adjust therapies in different inflammatory disease conditions, such as sepsis (Damas, P., et al. Crit. Care Med. 25, 405-412 (1997)), cancer (Lippitz, B. E. Lancet Oncol. 14, E218-E228 (2013)), lupus (Maczynska, I., et al. Immunol. Lett. 102, 79-82 (2006)), and graft-versus-host disease (GVHD) (Visentainer, J. E. L., et al. Exp. Hematol. 31, 1044-1050 (2003)). Given the complexity and dynamic nature of the human immune system, detection and trending of biomarker signatures and subtle changes occurring during a diseased state requires rapid analysis of a complex panel of multiple cytokines at high accuracy, sensitivity and throughput. However, conventional methods based on fluorescence sandwich immunoassays fall short of meeting this demand as they face stringent limitations on their practical implementation in an ideal immune monitoring approach. These limitations arise primarily due to the need for multiple time-consuming labeling and washing processes while consuming a large sample volume. At present, no assay exists that satisfies all the requirements of near-real-time immune status monitoring that involve analysis of complex biological samples.

Systems and methods for high-throughput immunoassays are needed.

SUMMARY

Provided herein are systems and methods for performing assays. In particular, provided herein are systems and methods for performing high throughput immunoassays.

Embodiments of the present disclosure provide multiplex capable LSPR immunoassays that meet a need for rapid (e.g., near real time), accurate immunoassays (e.g. for use in beside diagnostics). The LSPR assays are as accurate as existing ELISA assays but provide the advantage of increased speed and multiplex capability. In addition, the LSPR immunoassays are able to analyze small volumes of complex patient samples (e.g., serum).

For example, in some embodiments, the present disclosure provides a localized surface plasmon resonance device (LSPR), comprising: a) an array of metal spots (e.g., gold or other noble metal as a nanorods, sphere, pyramid, bipyramid, star or other shape) localized on e.g., glass or thermoplastic substrate, wherein the metal spots comprise antibodies specific for at least one polypeptide; and b) a plurality of microfluidic channels in fluid communication with the array. In some embodiments, the antibodies comprise a plurality (e.g., 2, 3, 4, 5, 6, 7, 8, 9, 10, or more) of antibodies, wherein each antibody is specific for a different polypeptide. In some embodiments, the polypeptides are cytokines, polypeptides, antibodies, or nucleic acids. In some embodiments, the cytokines are selected from, for example, interleukin-2 (IL-2); interleukin-4 (IL-4); interleukin-6 (IL-6); interleukin-10 (IL-10); interferon-gamma (IFN-$\gamma$); tumor-necrosis-factor alpha (TNF-$\alpha$) acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL-17, IL1A, IL1B, inflammasome, interferome, interferon, interferon beta 1a, interferon beta 1b, interferon gamma, interferon type I, interferon type II, interferon type III, interferon-stimulated gene, interleukin 1 family, interleukin 1 receptor antagonist, interleukin 12, interleukin 12 subunit beta, interleukin 13, interleukin 16, interleukin 2, interleukin 23, interleukin 23 subunit alpha, interleukin 34, interleukin 35, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, XCL1, XCL2, XCR1 Interleukin-1, Interleukin-1 receptor antagonist, Interleukin-2, Interleukin-2 receptor antagonist, Interleukin-4, Interleukin-6, Interleukin-8, Interleukin-10, Interleukin-12, Interleukin-17, Interluekin-23, Tumor necrosis factor alpha, Interferon gamma, Granzyme B, HSP1AB, MMP-8, MIP-1a, antibodies (e.g., monoclonal or polyclonal), nucleic acids (e.g., DNA, mRNA, miRNA, lncRNA), nucleic acid probes, Chemokine (c-c motif) ligand 3 (Macrophage inflammatory protein 1-alpha), Matrix metalloproteinase-8, or Heat shock protein 70 A1B. In some embodiments, the microfluidic channels are orthogonal to the array of metal particles. In some embodiments, the device comprises at least 5 (e.g., 10 or more) parallel microfluidic channels. In some embodiments, the microfluidic channels have a volume of approximately 10 nl to 10 µl (e.g., 50 to 500 nL). In some embodiments, each of the microfluidic channels has an inlet port and an outlet port. In some embodiments, the microfluidic channels are constructed of PDMS or thermoplastic. In some embodiments, the substrate comprises at least 100 (e.g., at least 200, at least 300, at least 400, at least 500, at least 750, or at least 1000) antibodies. In some embodiments, the substrate is treated with oxygen plasma, UV/ozone, or silanization. In some embodiments, the antibodies are attached to said substrate via linker (e.g., a C1-C10 bifunctional thiol linker).

In some embodiments, the substrate further comprises a plurality of microelectrodes configured for AC electroosmosis, wherein the microelectrodes are in operable communication with the array of metal particles. In some embodiments, each of the arrays of metal nanoparticles is in operable communication with a pair of microelectrodes. In some embodiments, the microelectrodes are configured to deliver alternating current.

Further embodiments provide a system, comprising a) any of the aforementioned devices; and b) a LSPR detection apparatus. In some embodiments, the system further comprises one or more of a sample handling component, a data analysis component, or a user interface. In some embodiments, the device is provided as a cartridge.

Additional embodiments provide a method of measuring levels of one or more polypeptides, comprising a) contacting the system described herein with a sample (e.g., a sample from a subject); and b) measuring the level of one or more polypeptides in the sample using LSPR. In some embodiments, the detection is multiplex detection of two or more distinct polypeptides. In some embodiments, the polypeptides are cytokines. In some embodiments, the sample is a biological sample (e.g., including but not limited to, serum, blood, urine, sputum, CSF, or saliva). In some embodiments, the level of the cytokines is indicative of the presence of an inflammatory response (e.g., in sepsis, cancer, lupus, or graft-versus-host disease (GVHD)), an immune response, organ damage, or infection in the subject. In some embodiments, the subject is undergoing chemotherapy, cell or gene based therapy, immunomodulation, or surgery. In some embodiments, the results of the measuring are used to determine a treatment course of action in the subject (e.g., administration of an immune suppressant, a drug that blocks the activity of a cytokine (e.g., etanercept and/or tocilizumab), anti-rejection drug (e.g., tacrolimus), or a drug comprising recombinant proteins (e.g., sargramostim and/or filgrastim). In some embodiments, the measuring is completed in 2 hours (e.g., 1 hour, 50 minutes, 45 minutes, 40 minutes, 35 minutes, 30 minutes, 25 minutes, 20 minutes, 15 minutes, 10 minutes, 5 minutes) or less.

Yet other embodiments provide a method of measuring levels of one or more cytokines in a biological sample from a subject, comprising: a) contacting the system described herein with a biological sample from a subject; and b) measuring the level of one or more polypeptides in the sample using LSPR.

Additional embodiments are described herein.

DEFINITIONS

Figure 1:
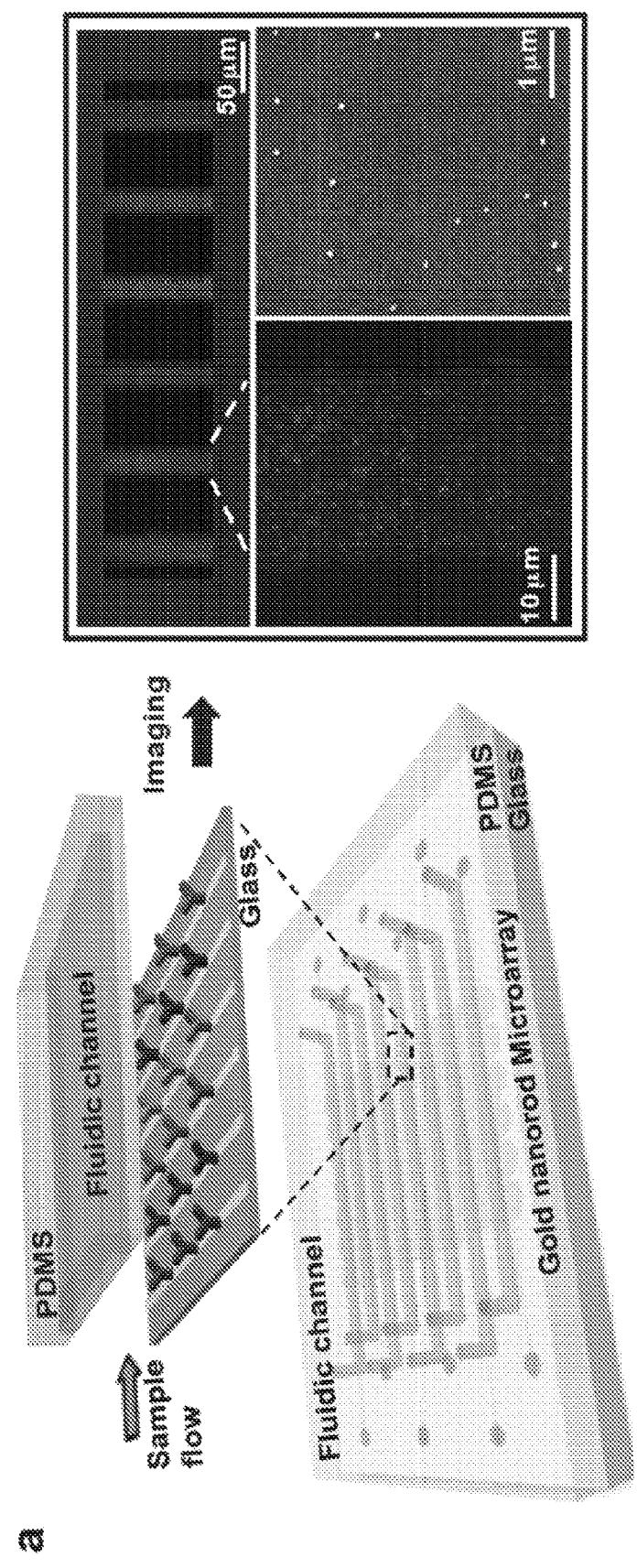
FIG. 1 shows a schematic and principle of exemplary immunoassays. (A) Schematic of the LSPRmi chip. (B) Histograms of the particle-to-particle distance of the AuNRs on the LSPRmi chip characterized using SEM images. (C) The principle of the LSPRmi method.
Figure 1:
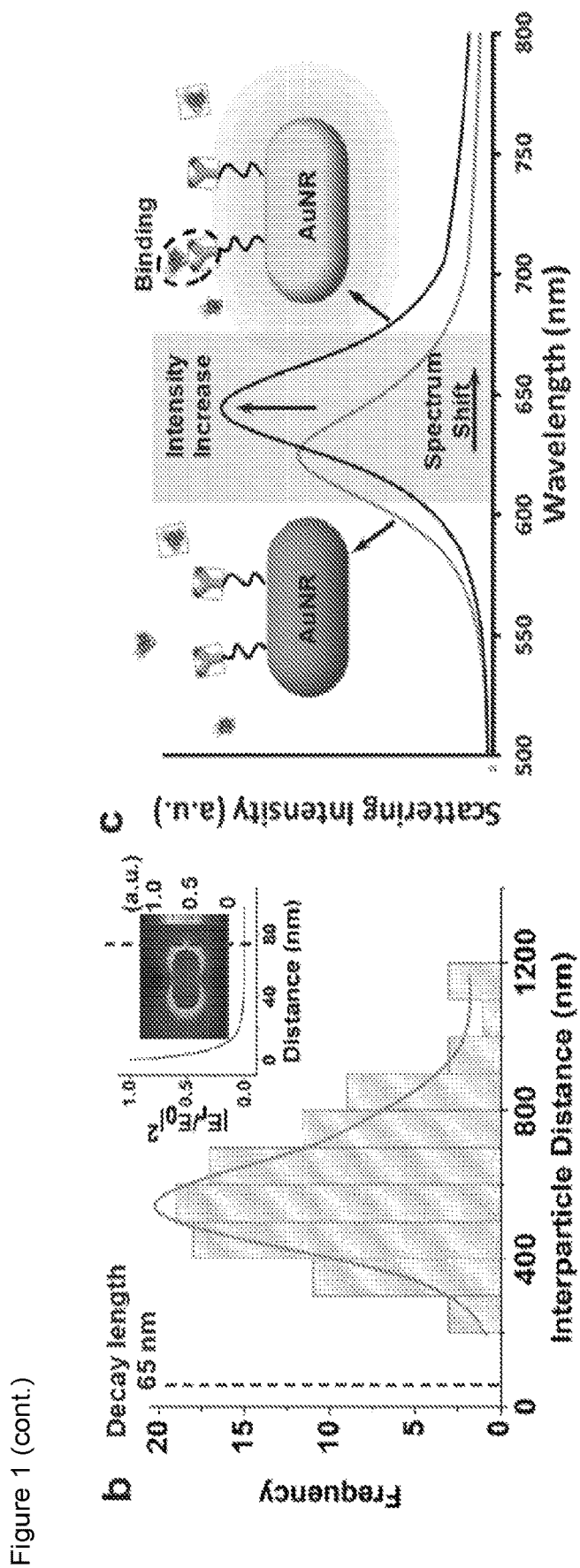

The term "assay reagents" as used herein is used in the broadest sense and refers to any reagent useful, necessary, or sufficient for performing the immunoassays of the present disclosure. Examples include, but are not limited to, antibodies, controls, buffers, calibration standards and the like.

The term "sample" in the present specification and claims is used in its broadest sense. It is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present disclosure.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

"Antigen binding molecule" refers to a molecule that binds a specific antigen. Examples include, but are not limited to, proteins, nucleic acids, aptamers, synthetic molecules, etc.

"Antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries.

"Specific binding" or "specifically binding" when used in reference to the interaction of an antibody and an antigen means that the interaction is dependent upon the presence of a particular structure (e.g., the antigenic determinant or epitope) on the antigen; in other words the antibody is recognizing and binding to a specific structure rather than to antigens in general. For example, if an antibody is specific for epitope "A," the presence of a protein containing epitope A (or free, unlabelled A) in a reaction containing labeled "A" and the antibody will reduce the amount of labeled A bound to the antibody.

As used herein, "microfluidic" refers to, for example, a device for transport or storage of small volumes (e.g., of liquids such as assay reagents). In some embodiments, individual channels or chamber of microfluidic devices comprise a volume of 10 nL to 1μL (e.g., 10, 20, 50, 100, 200, 300, 400, 500, or 750 nL), although other sizes are contemplated.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present disclosure.

DETAILED DESCRIPTION

Provided herein are systems and methods for conducting assays. In particular, provided herein are systems and methods for performing high throughput immunoassays.

LSPR is a plasmonic phenomenon that arises around nanoscale structures or nanoparticles of noble metal (e.g., ruthenium, cesium, palladium, silver, gold, iridium, platinum, gold, and combinations thereof) when light is illuminated onto a nanoscale featured sensing surface. When the incident light frequency matches the natural frequency of electron oscillation of the conductive metal nanoparticles, the interactions between the incident light and the nanostructured surface maximize the optical extinction of the particles with electrons highly enhanced near the particles' surfaces and trigger the LSPR. The resonance wavelength and intensity can be readily modified by the temporal or irreversible absorption of analyte as small as protein, nucleic acids and cytokines. As such, it has been proven to be an effective label-free detection method for antibody-antigen binding that permits high-sensitivity and real-time analysis. In addition, the elimination of secondary antibody labeling can significantly suppress cross-reactivity. Since the sensor elements used in LSPR technique can be as small as a few tens of nanometers in diameter, it provides a significant advantage in constructing a large number of sensor arrays integrated on a single chip, which enables a high-throughput, high multiplicity sensing platform with drastically reduced sample volume and total assay time.

Relying upon the measurement of labeling signals, conventional sandwich immunoassays often employed in ELISA provide the end-point analyte readout only after the completion of all the multiple reagent processes. Without precisely knowing the end-point timing, users of these assay techniques need to follow a protocol requiring two hours for the analyte incubation. Additional labeling and washing steps together with the time-consuming incubation process result in a total assay time of typically eight hours or longer. In contrast, both the label-free nature and real-time analyte binding monitoring capability demonstrated in the present disclosure provide the significant advantages. These features allowed for elimination of a multi-step assay processes and reduced the analyte incubation time to, for example, less than 30 min. From the real-time sensor signal saturation point, it was possible to determine the endpoint of the analyte-binding assay where the washing process could be initiated to remove the non-specifically adsorbed analyte molecules. This allowed the entire LSPRmi immunoassay involving the parallel sample loading, multi-analyte (IL-2, IL-4, IL-6, IL-10, TNF-α, and IFN-γ) binding, incubation, and washing across 480 on-chip biosensing spots to be completed within such a short period of time (e.g., 40 min). This assay time is more than ten times shorter than that of the conventional ELISA.

Despite the impressive rapidness, sample efficiency, and throughput, multi-arrayed LSPR biochip schemes in serum cytokine screening have faced a major issue in the past—the poor limit of detection (LOD). For instance, major efforts have been made to identify serum cytokine profiles useful for either the early detection of sepsis or to assess illness severity (Wong, H. R., et al. Critical Care 16, article R174

Figure 8:
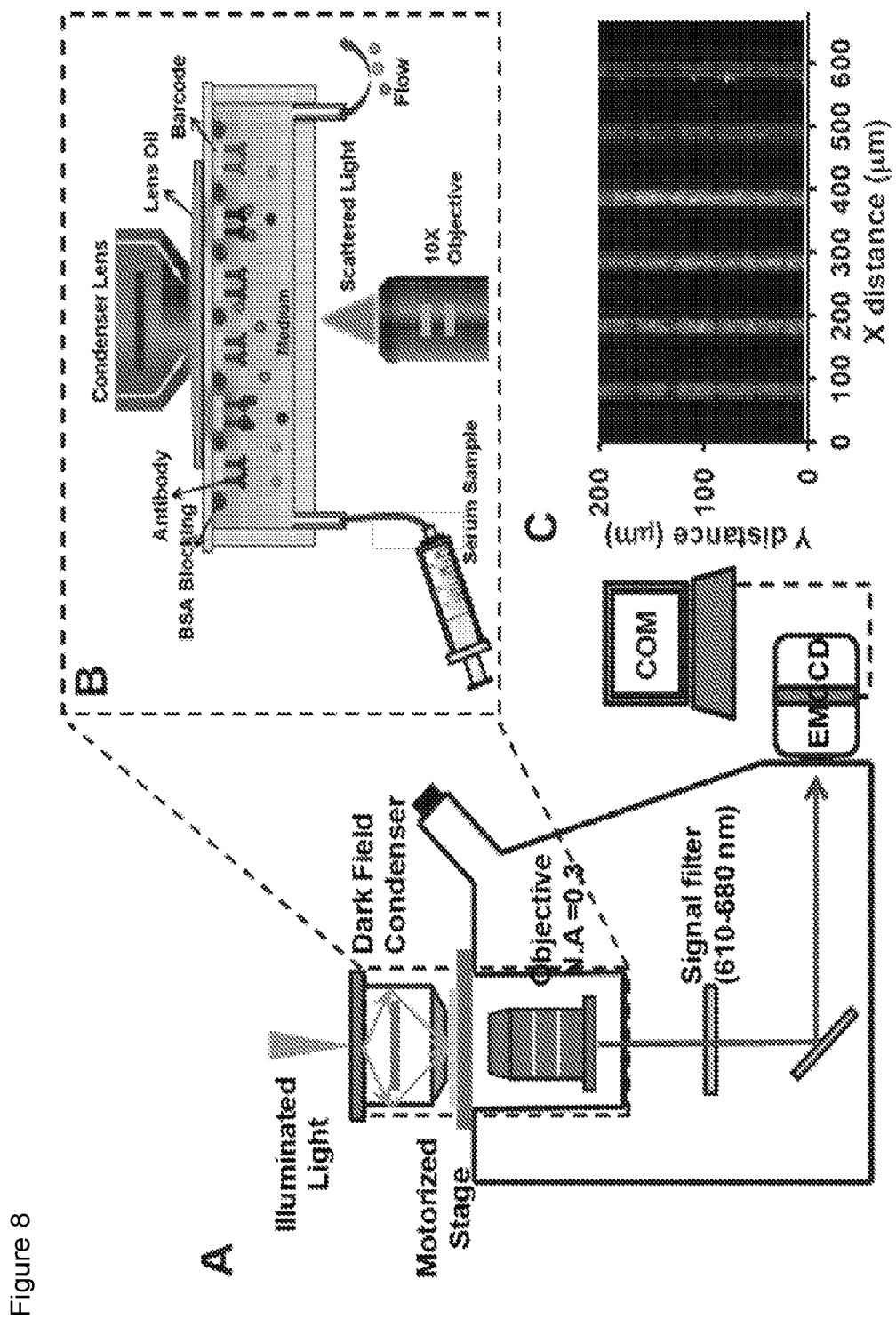
FIG. 8 shows (A) Schematic of the dark-field microscope setup for LSPRmi immunoassay. (B) Illustration of the LSPRmi assay protocol using the prepared LSPRmi chip and dark-field imaging. (C) Microarray images analyzed by customized Matlab program.

(2011); Bozza, F. A., et al. Critical Care 11, article R49 (2007)). Serum cytokine concentrations for patients with sepsis can vary widely necessitating both a wide dynamic range and low LOD to provide meaningful information with clinical utility. Bozza et al. report the ability to predict 28-day mortality in patients with sepsis by measuring serum IL-8 within the first 72 hours of admission (Bozza et al., supra). A serum IL-8 cutoff able to meaningfully discriminate between survivors and non-survivors with reasonable accuracy would be an assay capable of measuring serum cytokines concentrations <100 pg/mL. This cutoff value is already comparable to or far below the LOD's obtained by previous studies (Endo, T., et al. Anal. Chem. 78, 6465-6475 (2006); Acimovic, S. S., et al. Nano Lett. 14, 2636-2641 (2014)). To achieve such high sensitivity, embodiments of the detection method described herein employ dark-field imaging that scans the scattering light intensity across the LSPR biosensing spots (FIG. 8).

Nonspecific antibody cross-reactions pose significant challenges in retaining high accuracy for multiplex sandwich immunoassays. This issue becomes serious when the assay involves a large number of antibody pairs in a complex biological medium, such as human serum. It prevents the scaling up of multiplexing because non-specific bindings among antibodies, target analytes and other biological components in the solution (e.g., free plasma proteins, lipids, electrolytes, etc.) exponentially increase. The LSPR assay described herein overcomes these problems. It provides the additional advantage of the label-free nature of the LSPR biosensing scheme that eliminates the secondary antibody labeling. The direct measurement of the sensor response upon analyte binding substantially quenched the non-specific adsorption among all the biological species. As a result, the assay displayed a negligible cross-reactivity at cytokine concentrations of 500 pg/mL in human serum. The LSPRmi assay showed a significantly better correlation with single-plex ELISA than the commercial multiplex bead array assays (MBAA) for human serum analysis (Bozza, F. A., et al. Critical Care 11, article R49 (2007)).

Obtaining the serum samples from CPB-surgery pediatric patients, it was possible to exactly define the source of the inflammatory response of the hosts—the surgery and predict the anticipated assay outcomes. The LSPRmi assay successfully measured elevated cytokine levels, most notable for IL-6 and IL-10, in both neonates at 24 h after surgery for congenital heart disease using cardiopulmonary bypass. A very similar pattern to those previously reported where elevations in patient's serum cytokine levels most commonly return to pre-surgical levels within 48 hours of surgery was observed. Such information is valuable because very high and/or prolonged expression of both pro-inflammatory (e.g. IL-6) and anti-inflammatory (e.g. IL-10) cytokines are associated with the acute immune dysfunction following cardiopulmonary bypass and predict worse outcomes (Ashraf, et al., Eur. J. Pediatr. Surg. 12, 862-868 (1997); Seghaye, M. C., et al. J. Thorac. Cardiovasc. Surg. 111, 545-553 (1996)). The LSPR assay of embodiments of the present disclosure was capable of detecting variable degrees of responses in the two subjects after CPB. There are multiple mechanisms contributing to this variable cytokine expression (e.g., patient age, cardiac lesion, length of surgery and CPB, use of intraoperative steroids, etc.), however, no methodology exists to safely, routinely and repetitively measure serum cytokines in near real-time to enable clinicians to monitor a host inflammatory response and thereby alter therapeutic strategies as needed. The experiments described herein demonstrate the capability to routinely monitor multiple serum cytokines in patients using the LSPR assay. The rapid turn-around time (e.g., ~40 min), high sensitivity (e.g., down to ~6.46 pg/mL-20.56 pg/mL), extreme sample sparing ability (e.g., ~1 uL sample for six cytokines with 10 technical replicate measurements) and negligible cross-reactivity enable routine monitoring of serum cytokines with statistically high accuracy. Such characteristics provide use in monitoring a substantial number of different disease states—particularly in infants and neonates where sample volume has been a mitigating factor. Such key characteristics do not exist with current methods as the assay turn-around time and blood volume required make them impractical to use, especially in small infants.

Accordingly, provided herein is a multi-arrayed LSPR microarray (LSPRmi) device for parallel (e.g., massively parallel) high-throughput detection of multiple cytokine biomarkers in serum. Exemplary devices, systems, and methods are described herein.

I. Devices and Systems

Embodiments of the present disclosure provide devices and systems for use in LSPR immunoassays. In some embodiments, devices comprise a LSPR component and a microfluidic component. Exemplary devices are shown in FIG. 1. The present disclosure further provides systems for performing LSPR using the described devices.

A. LSPR surfaces

In some embodiments, devices comprise a LSPR component comprising a solid surface functionalized with a metal. In some embodiments, the solid surface is glass. Glass substrates offer good optical properties for imaging and surface modification capacity for surface function. Alternative surfaces include, but are not limited to, transparent plastics, such as poly(methyl methacrylate) (PMMA), known as acrylic glass, a transparent thermoplastic that can be modified with surface moieties for antibody function; polycarbonate; cyclic olefin copolymer (COC); cyclo olefin polymer (COP); polystyrene; polypropylene; and polyethylene terephthalate glycol-modified (PEGT).

In some embodiments, substrates are coated with metals that allow for the resonant oscillation of conduction electrons at the interface between a negative and positive permittivity material stimulated by incident light. This can occur as deposition of bulk material allowing detection of surface plasmon resonance (SPR), or as described herein as discrete plasmonic nanoparticles allowing detection of localized plasmon resonance (LSPR). Metals that support surface plasmons include, but are not limited to, silver, gold, copper, titanium or chromium. In some embodiments metals are provided as localized nanotubes or other geometric configurations. In some exemplary embodiments (See e.g., FIG. 1), metal nanorods or other metal configurations are arranged in stripes or other regular patterns on the surface (See e.g., Williams S E, Davies P R, Bowen J L, and Allender C J. Controlling the nanoscale patterning of AuNPs on silicon surfaces. Nanomaterials 2013; 3: 192-203; herein incorporated by reference in its entirety). In addition to nanorods, other suitable particle configurations include, but are not limited to, nanospheres, nanostars, nanodiamonds, nanopyramids, nanobipyramids, or nanorings and metal core-shell structures (e.g., gold/silver core-shell structures). Silver exhibits good optical properties but may be toxic in a biological environment due to the release of silver ions. The chemically inert gold nanoshell provides biocompatibility while maintaining the extraordinary optical properties of the silver core. In some embodiments, other noble metals are utilized (e.g., ruthenium, rhodium, palladium, osmium, iridium, platinum).

In some embodiments, metallic surfaces or areas are functionalized with antibodies (e.g., monoclonal or polyclonal antibodies) that bind to a specific peptide or polypeptide (e.g., antigen). The present disclosure is not limited to particular antibodies. In some embodiments, antibodies are specific for a cytokine or chemokine (e.g., one or more of interleukin-2 (IL-2); interleukin-4 (IL-4); interleukin-6 (IL-6); interleukin-10 (IL-10); interleukin-(IL-8); interleukin-12 (IL-12) interferon-gamma (IFN-γ); or tumor-necrosis-factor alpha (TNF-α)). Additional cytokines include, but are not limited to, acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL-17, IL1A, IL1B, inflammasome, interferome, interferon, interferon beta 1a, interferon beta 1b, interferon gamma, interferon type I, interferon type II, interferon type III, interferon-stimulated gene, interleukin 1 family, interleukin 1 receptor antagonist, interleukin 12, interleukin 12 subunit beta, interleukin 13, interleukin 16, interleukin 2, interleukin 23, interleukin 23 subunit alpha, interleukin 34, interleukin 35, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, XCL1, XCL2, and XCR1.

Additional suitable analytes include, but are not limited to, Interleukin-1, Interleukin-1 receptor anatagonist, Interleukin-2, Interleukin-2 receptor antagonist, Interleukin-4, Interleukin-6, Interleukin-8, Interleukin-10, Interleukin-12, Interleukin-17, Interluekin-23, Tumor necrosis factor alpha, Interferon gamma, Granzyme B, HSP1AB, MMP-8, MIP-1a, antibodies (e.g., monoclonal or polyclonal), nucleic acids (e.g., DNA, mRNA, miRNA, lncRNA), nucleic acid probes, Chemokine (c-c motif) ligand 3 (Macrophage inflammatory protein 1-alpha), Matrix metalloproteinase-8, and Heat shock protein 70 A1B.

In some embodiments, linkers are utilized to attach antibodies to surfaces (e.g., using carbodiimide (e.g., EDC (1-Ethyl-3-(3-dimethylaminopropyl)-carbodiimide))/NHS chemistry). In some embodiments, linker is a bifunctional thiol linker. The present disclosure is not limited to the length of the linker. In some embodiments, the linker comprises a 1 to 10 carbon atom chain (e.g., 1, 2, 3, 4, 5, 6, 7, 8, 9, or 10 carbons).

In some embodiments, multiplex detection is enabled by providing distinct antibodies in addressable locations on the array surface (e.g., by physically addressed barcodes). For example, in some embodiments, individual rows or channels each contain one specific antibody (e.g., at shown in FIG. 1A). This provides a barcode array that allows for multiplexing by assigning distinct antibodies to specific locations (e.g., spots or dots) on the array.

Surfaces (e.g., glass or thermoplastic surfaces) are generated using any suitable method. In some embodiments, the method described in Example 1 is utilized. For example, in some embodiments, the substrate is treated with oxygen plasma, UV/ozone, and metal nanorods or other metal component are patterned using a microfluidic patterning technique through electrostatic interactions between the metal and the glass surface. In some embodiments, the constructed metal patterns are functionalized (e.g., with thiolated alkane 10-Carboxy-1-decanethiol (HS-(CH2)10-COOH)) through ligand exchange and subsequently activated for antibody attachment using standard EDC/NHS coupling chemistry.

Other suitable protocols for functionalizing surfaces include, but are not limited to, APTES functioned glass or thermoplastic covalently interact with gold nanorods (Kathryn Mayer et. al., *ACS Nano*, 2, 687-692, 2008; herein incorporated by reference in its entirety); Silane functioned surfaces covalently interact with citrate stabilized god nanoparticles (Maniraj Bhagawati et. al. *Anal. Chem.*, 85, 9564-9571, 2013; herein incorporated by reference in its entirety); and random deposited CTAB gold nanorods with aptamers for detection (Christina Rosman et.al. Nano Lett. 13, 3243-3247, 2013; herein incorporated by reference in its entirety).

In some embodiments, surfaces are silanized (See e.g., Haddada M B, et al. Gold Bull 2013; 46: 335-341; Cant N E, et al. Thin Solid Films 2003; 426: 31-39). In some embodiments, silanes are aminated, thiolated, or disulfide modified. In some embodiments, silanization is performed via chemical vapor deposition (e.g., plasma-enhanced CVD or low pressure CVD or via protic solvent).

Figure 13:
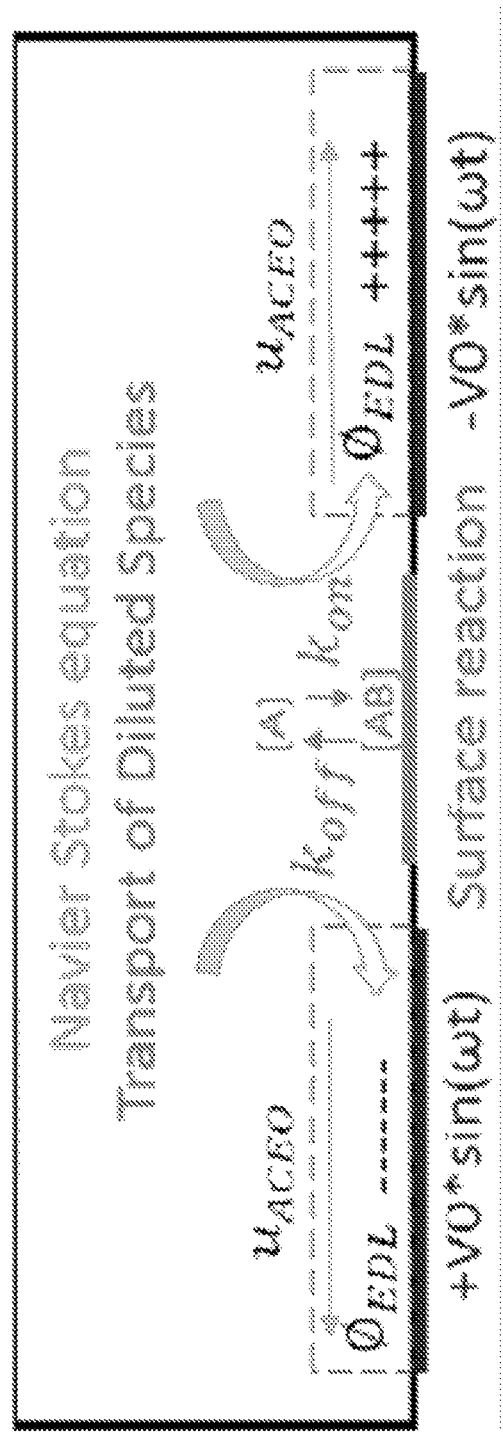
FIG. 13 shows a schematic of ACEO flow and its effect on surface reaction.

In some embodiments, surfaces comprise AC electroosmosis (ACEO) components. ACEO is a nonlinear electrokinetic phenomenon of induced-charge electroosmotic flow around electrodes when applying an alternating voltage. The polarization of the electrode surface induces a diffuse ion layer called electrical double layer (EDL) (See, e.g., FIG. 13). At a given frequency, the electrical potential at the outer edge of the EDL causes a tangential electrical field, which exerts a non-zero time-averaged outward direction (as shown by the green arrows on the electrode surface) force on the induced charge (EDL). This movement of EDL leads to a circumferential fluid motion inside the microfluidic channel and can work as a micropump to facilitate the transportation of analytes down to the sensing surface. Therefore, the depletion zone formed under a diffusion-limit regime can be significantly reduced by ACEO. The surface reaction rate is thus greatly enhanced due to this continuous fluid motion, especially for ultra-low concentration biomarker detection. Accordingly, in some embodiments, devices further comprise a plurality of microelctrodes configured for ACEO in communication with the arrays of metal particles. In some embodiments, each array (e.g., nanotube) is attached to a plurality of electrodes.

B. Microfluidic Component

In some embodiments, devices of embodiments of the present disclosure comprise a microfluidic component. The microfluidic component is in fluid communication with the LSPR component and serves to transport assay components (e.g., patient samples and assay reagents) to the LSPR component. In some embodiments, the microfluidic component comprises a plurality (e.g., 2, 4, 6, 8, 10, 12 or more depending on the size of the device) of microfluidic channels. In some embodiments, channels have outlet and inlet components and/or reservoir components for supplying fluids to regions the device. In some embodiments, microfluidic channels are placed perpendicular to LSPR patterned components.

The microfluidic component is constructed of any suitable material. In some embodiments, layers are made by supplying a negative "master" and casting a castable material over the master. Castable materials include, but are not limited to, polymers, including epoxy resins, curable polyurethane elastomers, polymer solutions (e.g., solutions of acrylate polymers in methylene chloride or other solvents), curable polyorganosiloxanes, and polyorganosiloxanes which predominately bear methyl groups (e.g., polydimethylsiloxanes ("PDMS")). Curable PDMS polymers are well known and available from many sources. Both addition curable and condensation-curable systems are available, as also are peroxide-cured systems. All these PDMS polymers have a small proportion of reactive groups which react to form crosslinks and/or cause chain extension during cure. Both one part (RTV-1) and two part (RTV-2) systems are available.

In some embodiments, transparent devices are desirable. Such devices may be made of glass or transparent polymers. PDMS polymers are well suited for transparent devices. A benefit of employing a polymer that is slightly elastomeric is the case of removal from the mold and the potential for providing undercut channels, which is generally not possible with hard, rigid materials. Methods of fabrication of microfluidic devices by casting of silicone polymers are well known. See, e.g. D. C. Duffy et al., "Rapid Prototyping of Microfluidic Systems in Poly(dimethylsiloxane)," Analytical Chemistry 70, 4974-4984 (1998). See also, J. R. Anderson et al., Analytical Chemistry 72, 3158-64 (2000); and M. A. Unger et al., Science 288, 113-16 (2000), each of which is herein incorporated by reference in its entirety.

In some embodiments, fluids are supplied to the device by any suitable method. Fluids may, for example, be supplied from syringes, from microtubing attached to or bonded to the inlet channels, etc.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. Integration of passively-driven pumping systems and microfluidic channels is described by B. H. Weigl et al., Proceedings of MicroTAS 2000, Enshede, Netherlands, pp. 299-302 (2000).

In some embodiments, fluid flow is established by a gravity flow pump, by capillary action, or by combinations of these methods. A simple gravity flow pump consists of a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

To obtain constant flow, a gravity-driven pump as disclosed in published PCT application No. WO 03/008102 A1 (Jan. 18, 2002), herein incorporated by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective channel or reservoir will exhibit greater capillary forces with respect to its channel or reservoir walls as compared to the capillary forces in the associated device. This difference in capillary force may be brought about by several methods. For example, the walls of the outlet and inlet channels or reservoirs may have differing hydrophobicity or hydrophilicity. Alternatively, the cross-sectional area of the outlet channel or reservoir is made smaller, thus exhibiting greater capillary force.

In some embodiments, construction of fluidic devices is by soft lithography techniques as described for example by Duffy et al (Analytical Chem 70 4974-4984 1998; See also Anderson et al, Analytical Chem 72 158-64 2000 and Unger et al., Science 288 113-16 2000). Addition-curable RTV-2 silicone elastomers such as SYLGARD® 184 Dow Corning Co can be used for this purpose. The dimensions of the channels are readily determined by volume and flow rate properties etc.

The substrate may be of one layer or plurality of layers. The individual layers may be prepared by numerous techniques including laser ablation, plasma etching, wet chemical methods, injection molding, press molding, etc. Casting from curable silicone is most preferred, particularly when optical properties are important. Generation of the negative mold can be made by numerous methods all of which are well known to those skilled in the art. The silicone is then poured onto the mold degassed if necessary or desired and allowed to cure. Adherence of multiple layers to each other may be accomplished by conventional techniques.

A method of manufacture of some devices employs preparing a master through use of negative photoresist SU-8 50 photoresist from Micro Chem Corp Newton Mass.

In some embodiments, devices are injection molded. For example, in some embodiments, devices comprise injection molded thermoplastic fluidic layers bonded to the detection substrate.

C. Systems

In some embodiments, LSPR signals are detected by any suitable detector. An exemplary detector is shown in FIG. 8. In some embodiments, devices are placed on a movable platform or stage for scanning multiple locations on the device. In some embodiments, detectors comprise a light source, one or more objectives, filters, dark field condensers, and imaging components (e.g., CCD detectors).

In some embodiments, devices are configured for multiplex detection of multiple polypeptides. For example, as described above, a bar code component is provided by providing specific distinct antibodies in addressable locations on the LSPR surface.

Figure 3:
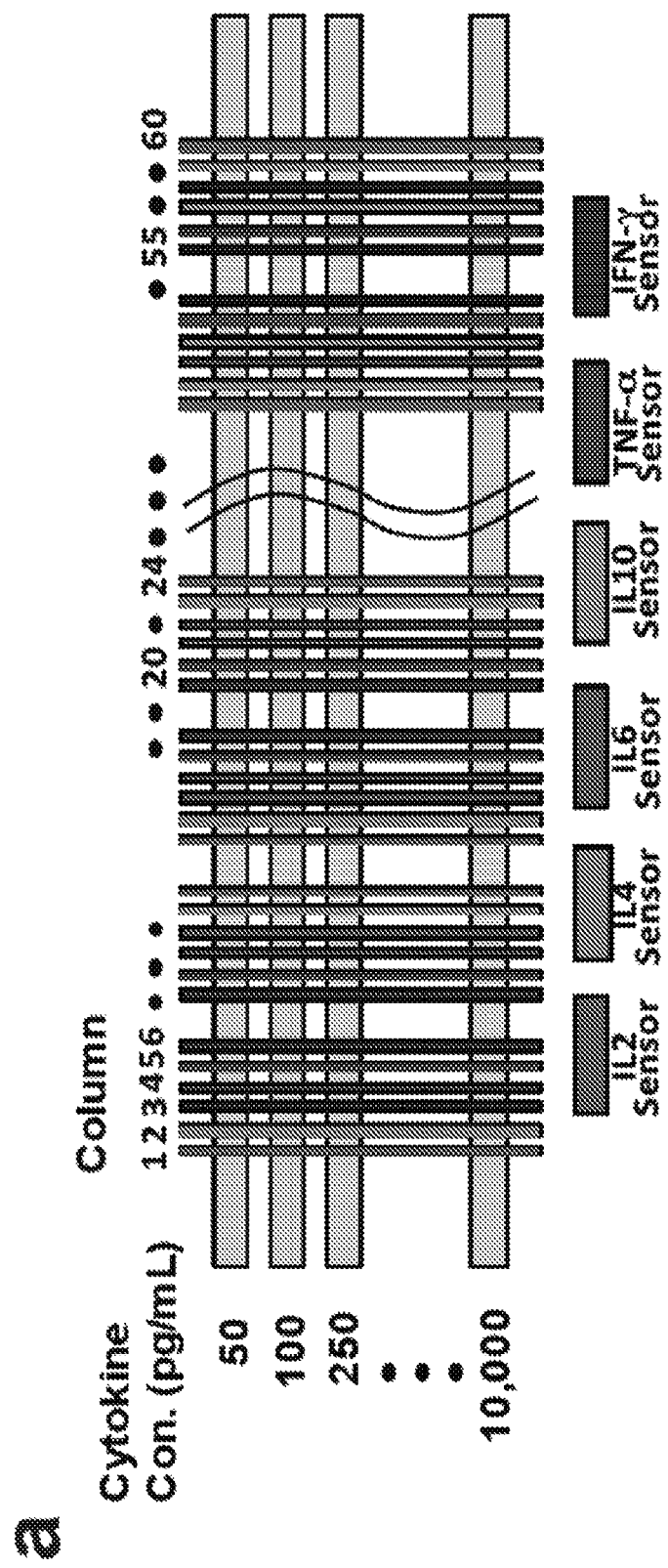
FIG. 3 shows LSPRmi intensity mapping and calibration curves. (A) LSPRmi chip layout consisting of 60 antibody-functionalized AuNR stripes segmented by 8 microfluidic detection channels. (B) Mapping of LSPR signal intensity shifts over the 480 AuNR barcode sensor spots on the LSPRmi chip obtained by the multi-analyte calibration process for the six cytokines in a). (C) Calibration curves of TNF-α, IFN-γ, IL-2, IL-4, IL-6, IL-10 obtained from the LSPR barcode intensity mapping in (B).
Figure 3:
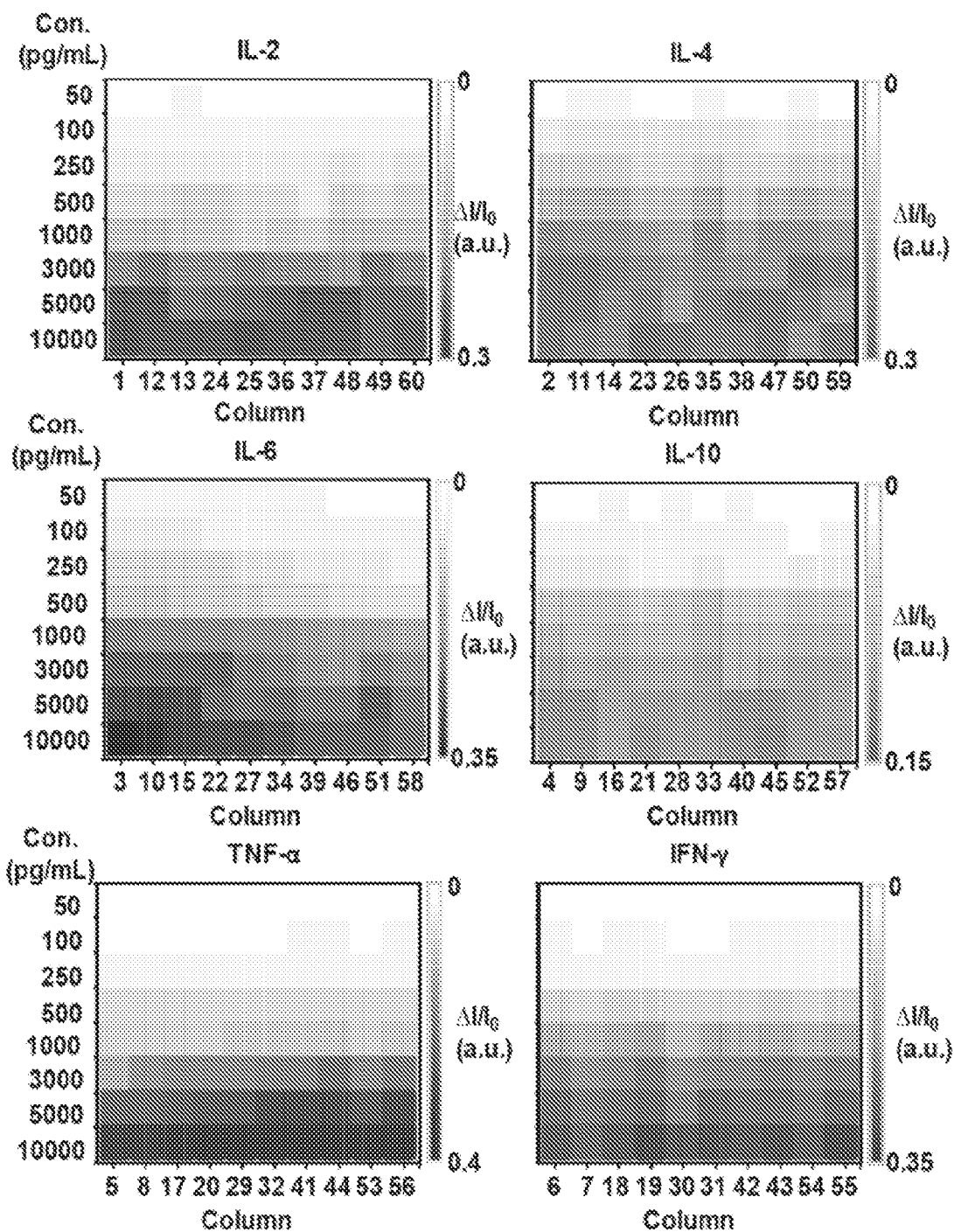
Figure 3:
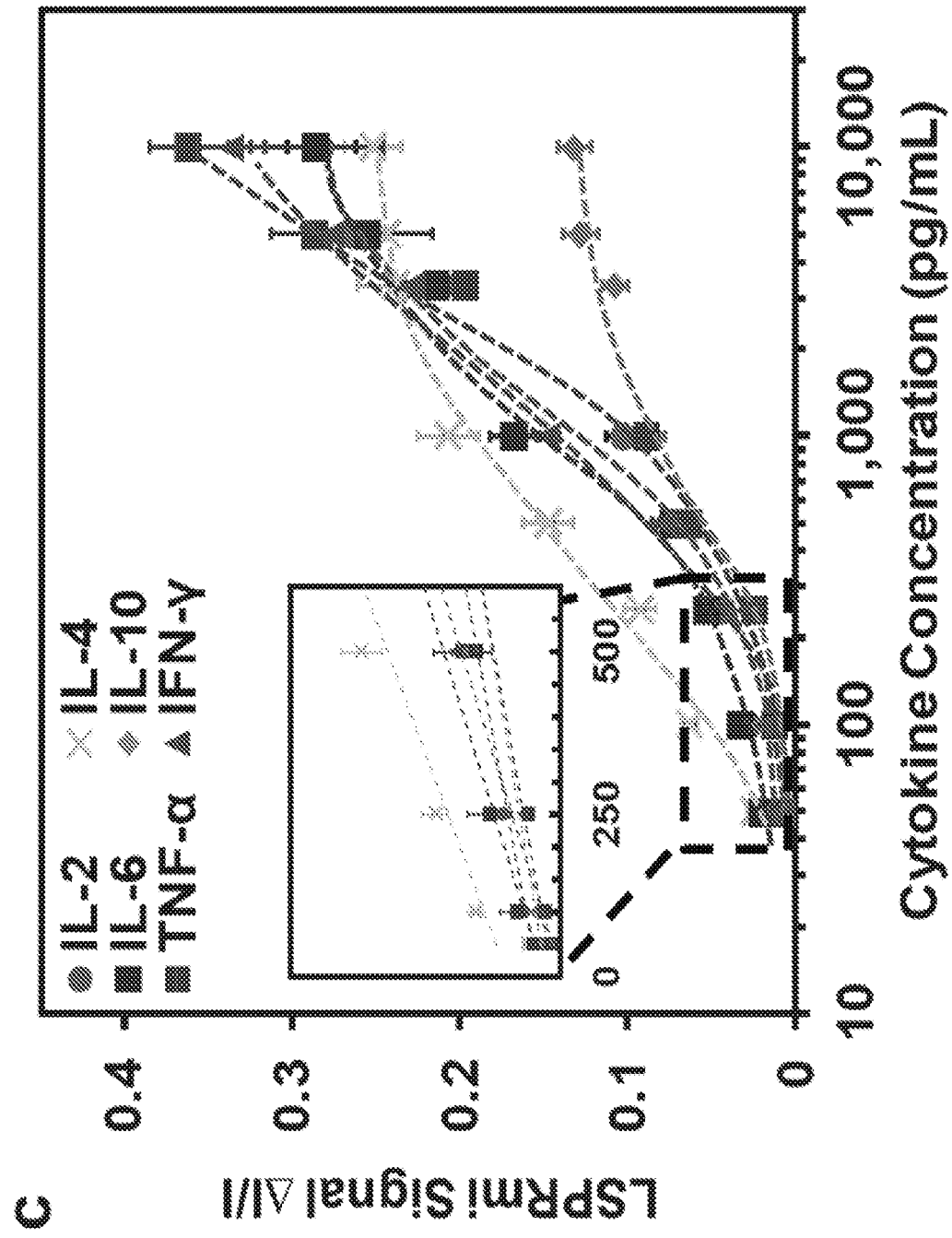

In some embodiments, following imaging, a software component is utilized to analyze signal from the array. For example, in some embodiments, software is configured to process an image, determine which locations have target antigen bound, and provide a report. In some embodiments, binding data is quantitative. For example, in some embodiments, a calibration curve is obtained prior to performing the assay (See e.g., FIG. 3) and/or in parallel on each chip (e.g., as internal positive and negative controls).

Figure 18:
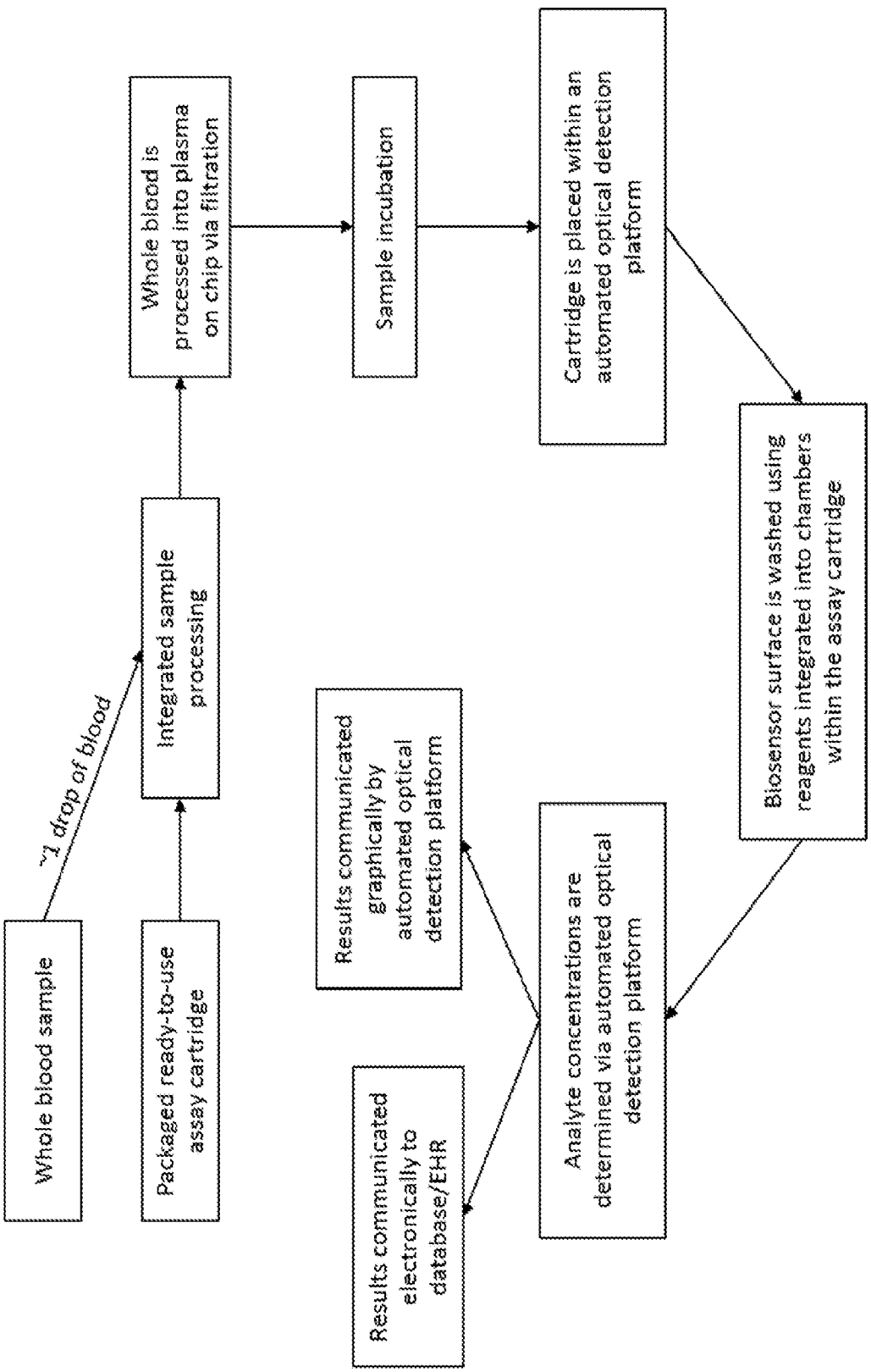
FIG. 18 shows a workflow for an exemplary analysis system of embodiments of the present disclosure.

In some embodiments, systems are automated. For example, in some embodiments, systems (See e.g., FIG. 18) comprise one or more of a packaged, ready to use cartridge (LSPR chip), integrated sample processing component (e.g., robotic sample handling system), automated optical detection platform (e.g., those described herein), and computer-based sample analysis and display component (e.g., display screen, tablet, smart phone, etc.).

In some embodiments, a computer-based analysis program is used to translate the raw data generated by the detection assay (e.g., the presence, absence, or level of an antigen) into data of predictive value for a clinician (e.g., choice of therapy). The clinician can access the predictive data using any suitable means. Thus, in some preferred embodiments, the present disclosure provides the further benefit that the clinician, who is not likely to be trained in immunology or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., a blood, urine or serum sample) is obtained from a subject and submitted to a profiling service (e.g., clinical lab at a medical facility, profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., levels of antigens), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of organ rejection or immune response) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

In some embodiments, systems comprising devices, detectors, software, and computer components (e.g., computer processor and display screen, smart phone, etc.) are provided. In some embodiments, the detection and analysis components are provided as a platform and the devices are provided as cartridges or plates (e.g., disposable or re-usable devices). For example, in some embodiments, the portion of the system that contacts patient sample is provided as a disposable cartridge or strip and the detection and analysis platform is a stand-alone reusable component that can accept and analyze cartridges specific for one or more target antigens.

In some embodiments, the entire system is provided as a hand held device (e.g., suitable for bedside use). In some embodiments, handheld devices comprise a disposable strip or cartridge for patient sample. In some embodiments, handheld devices are target specific (e.g., dedicated to a specific antigen) or target independent (e.g., suitable for accepting different cartridges or strips specific for different antigens).

II. Methods

Embodiments of the present disclosure provide the use of the devices and systems described herein for detection of antigens (e.g., in patient samples). In some embodiments, the entire assay is completed in one hour (e.g., 50 minutes, 40, minutes, 30 minutes, 20 minutes, 10 minutes, 5 minutes, 4 minutes, 3 minutes, 2 minutes, 1 minute, etc.) or less. This provides a distinct advantage over traditional ELISA assays, which often require multiple hours to complete. Such rapid assays are especially useful in patient care settings where decisions about treatment and interventions need to be made rapidly.

The present disclosure is not limited to particular patient samples. Examples include, but are not limited to, serum, whole blood, urine, sputum, semen, cerebral spinal fluid (CSF), or saliva. In some embodiments, samples are processed or purified prior to use. In some embodiments, samples are utilized without processing (e.g., from a finger prick or urine sample). In some embodiments, sample volumes are 1 µL or less (e.g., 900 nL, 800 nL, 700 nL, 600 nL, 500 nL, 400 nL, 300 nL, 200 nL, or 100 nL or less).

In some embodiments, the present disclosure provides methods for detecting one or more cytokines (e.g., those disclosed herein), chemokines, or other makers of inflammation, immune response, organ damage, or infection. In some embodiments, the presence and/or levels of the cytokines in the sample is used to determine the presence of an inflammatory response, an immune response, organ damage, or infection in the subject. The present disclosure is not limited to particular inflammatory or immune responses. Examples include, but are not limited to, surgical trauma, sepsis, cancer, lupus, graft versus host disease (GVHD), autoimmune hepatitis, multiple sclerosis, systemic lupus erythematosus, myasthenia gravis, Type I diabetes, rheumatoid arthritis, psoriasis, Hashimoto's thyroiditis, Grave's disease, ankylosing spondylitis, Sjogrens disease, CREST syndrome, scleroderma, Crohn's disease, acute respiratory distress syndrome (ARDS), patients who have under gone solid organ transplants and are receiving immunosuppression therapy, ulcerative Colitis, polyarteritis nodosa, Whipple's disease, primary sclerosing cholangitis, etc.

In some embodiments, the subject is undergoing chemotherapy or has undergone surgery. In some embodiments, the levels of the cytokines are used to determine a treatment course of action. For example, in a patient found to be undergoing GVHD, sepsis, or an inflammatory response, an immune suppressant drug (e.g., steroid) or immune modulating drug (e.g., filgrastim) is administered.

In some embodiments, patients undergoing chemotherapy (e.g., chimeric antigen receptor T-cell therapy (CAR T-cell)), which results in release of cytokines, are monitored to measure cytokine levels. The levels of the cytokines are monitored to determine when patients have cytokine levels that are clinically too high (e.g., result in shock and/or hemodynamic instability). Such patients are administered anti-cytokine therapy (e.g., etanercept and/or tocilizumab). In some embodiments, cytokine levels are monitored to determine when levels have decreased sufficiently to reduce or halt therapy. In some embodiments, patients that do not have elevated levels of cytokines are not administered anti-cytokine therapy.

In some embodiments, patients are monitored (e.g., using bedside devices) multiple times during the course of treatment, recovery from surgery, or after treatment with an immune suppressing drug to determine if changes in treatment are needed. For example, in some embodiments, patient found to need immune suppressing therapy are monitored to determine when the inflammation or GVHD has subsided in order to determine that a decrease in dosage or discontinuation of treatment is advisable.

EXPERIMENTAL

Example 1

Methods

LSPRmi chip fabrication: Positively charged AuNRs (CTAB coating) used in this study were purchased from Nanoseedz. The AuNRs were patterned on an oxygen plasma treated glass substrate using a microfluidic patterning technique through electrostatic interactions between the AuNRs and the glass surface. The constructed AuNR barcode patterns were functioned with thiolated alkane 10-Carboxy-1-decanethiol (HS-$(CH_2)$10-COOH) through ligand exchange and subsequently activated using standard EDC/NHS coupling chemistry. The probe cytokine antibodies were then loaded into individual patterning channel forming a barcode array consisting of six parallel stripes each functioned with distinct antibodies to afford multiplexed detection of 6 different cytokines at one time.

LSPRmi assay protocol: The prepared LSPRmi assay chip was mounted on the motorized stage (ProScanIII, Prior Scientific, Rockland, Mass.) that allowed for 3D positioning and automated image scanning. The back of the glass substrate of the chip was attached with a dark-field condenser (NA=1.45, Nikon) via the lens oil. 250 nL sample was injected from the inlet, flown through the sample channel, and collected from the outlet. The light scattered from the barcodes was collected by the 10× objective lens beneath the assay chip, filtered by a band pass filter (610-680 nm), imaged by an electron-multiplying CCD (EMCCD, Photometrics, Tucson, Ariz.) camera and recorded using the NIS-Element BR analysis software. The obtained images were then analyzed by a customized Matlab program. Before each measurement, ~10 mins was elapsed to establish temperature stabilization of EMCCD to minimize the background signal drift.

LSPRmi assay human serum matrix multiplex performance characterization. To characterize both the multiplex capability and the assay's performance three separate mixtures of cytokines was used. One mixture contained a single cytokine species (TNF-a), one containing three analytes (IL-4, IFN-γ, and TNF-α), and finally one containing all six cytokines (IL-2, IL-4, IL-6, IL-10, IFN-γ, and TNF-α). Recombinant cytokines (Life Technologies, Frederick, Md.) were spiked into a commercially available heat-inactivated, charcoal absorbed human serum matrix to remove trace levels of cytokines (EMD Millipore, St. Charles, Mo.).

LSPRmi assay performance comparison to 'gold standard' ELISA. All six cytokines (IL-2, IL-4, IL-6, IL-10, IFN-γ, TNF-α) were spiked into healthy donor human serum obtained via venipuncture following informed written consent. The study was approved by the University of Michigan Institutional Review Board. Serum was obtained via venipuncture into vacutainer tubes containing clot activator (BD Diagnostics, Franklin Lake, N.J.). Tubes were processed according to the manufacturer's instructions. Serum samples doped with all six cytokines were diluted further with healthy donor serum to obtain samples across the entire dynamic range of the LSPRmi assay (32 pg/mL-5,000 pg/mL). Serum cytokine concentrations were quantified using the LSPRmi assay and compared to commercially available ELISA kits (IL-6, IL-10, IFN-γ, TNF-α, BioSource Europe S.A., Nivelles, Belgium; IL-2, IL-4, Thermo-Fisher Scientific, Rockford, Ill.).

LSPRmi assay for Serum cytokine quantification of pediatric patients following open-heart surgery with cardiopulmonary bypass. All studies described here were approved by the University of Michigan Institutional Review Board and conducted following informed parental consent. Briefly, two patients enrolled in an ongoing clinical trial for serum cytokine quantification were selected. Serum samples were collected prior to surgery, and then on post-operative days one, two, three, and four (Pre, D1, D2, D3, and D4 respectively), using SST microtainer (BD Diagnostics) according to the manufacturer's instructions. Serum cytokines (IL-2, IL-4, IL-6, IL-10, IFN-γ, TNF-α) were quantified using the LSPRmi immunoassay as described above.

Figure 9:
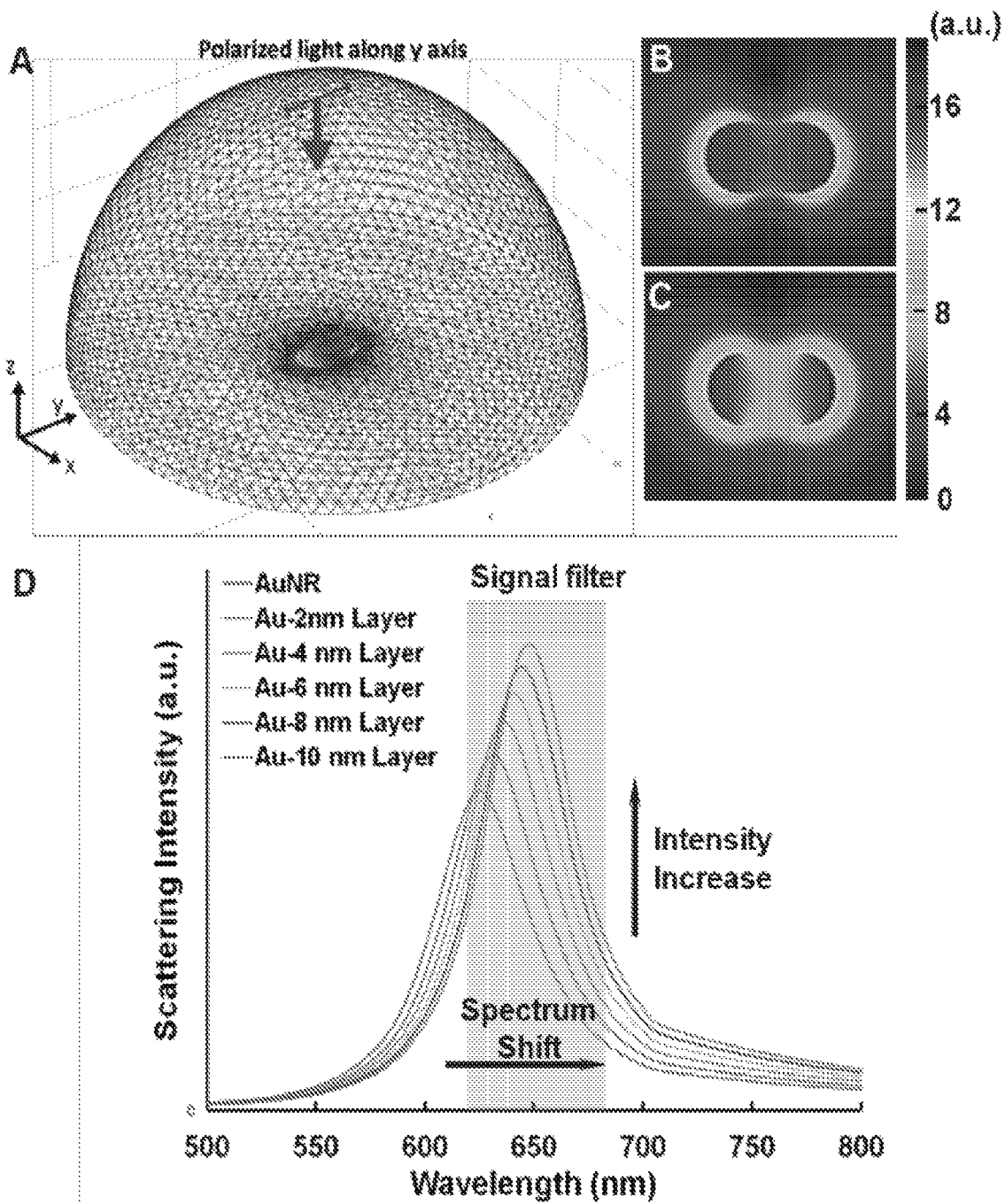
FIG. 9 shows A) FDTD simulation scheme on light scattering response from one single AuNR. B) Near-field LSPR intensity profile of a bare single AuNR excited by incident light. D) Predicted scattering spectrum (or LSPR spectrum) variation with the thickness of the protein coating on the AuNR.

FDTD simulations: The optical simulations to calculate the scattering efficiency on a single AuNR were performed using commercial multi-physics simulation software, COMSOL. In the simulation, the dimensions of the AuNR were set according to the results from the material characterization (40 nm in diameter, aspect ratio: 2). The frequency-dependent complex permittivity of gold was derived from Lorenze-Drude model. The far-field domain was defined as a spherical shell surrounding the AuNR with a radius identical with half the wavelength of incident light. The boundary condition was set to be a perfectly matched layer. The wave vector and electric field polarization of the incident light wave were set to be perpendicular and parallel to the orientation of the An. The mesh size was set to be 1 nm on the AuNR surface and no larger than ⅒ of the studied wavelength elsewhere. The spatial distribution of the electromagnetic field on the far-field plane was measured at varying frequencies with and without the presence of the AuNR to determine the intensity of scattering wave from the AuNR. FDTD simulations were performed by modeling the AuNR with dielectric layers mimicking the antibody/analyte binding. The calculated scattering spectrum for the bare AuNR and coated AuNR can be found in FIG. 9.

Characterization of gold nanorods. Gold nanorods (AuNRs) used in this study (FIG. 5A) were purchased from NanoSeedz in aqueous etrimonium bromide (CTAB, 0.1 M) buffer. These nanorods were originally synthesized using the standard seed-mediated growth method. This yielded single crystalline nanoparticles with an average length of 80±5 nm and an average width of 40±3 nm. (FIG. 5B) The CTAB coating on the AuNRs resulted in a positively charged surface with a zeta potential of 42±5 mV (Zetasizer Nano ZS90, Malvern). The extinction spectrum of the AuNRs in solution was obtained using a customized spectrophotometer. (Oh, B. et al. ACS Nano 8, 2667-2676 (2014)). The resonance peak wavelength of the AuNR lays around 626 nm, in consistent with the simulation results as shown below.

Gold nanorod microarray fabrication. Prior to the AuNR microarray fabrication, a microfluidic flow-patterning mask layer made of PDMS was constructed using soft lithography. The mask layer contains multiple sets of parallel microfluidic channels for patterning the AuNR microarrays. Specifically, a mold for the PDMS flow-patterning mask layer was patterned within a silicon substrate using deep reactive-ion etching (DRIE) (Deep Silicon Etcher, Surface Technology Systems, Allenton, Pa.). The mold surface was silanized with (tridecafluoro-1,1,2,2,-tetrahydrooctyl)-1-trichlorosilane vapor (United Chemical Technologies) for 1 hour in vacuum to facilitate subsequent PDMS release. PDMS prepolymer (Sylgard-184, Dow Corning), prepared by thoroughly mixing a curing agent with a base monomer (wt:wt=1:10) was poured onto the silicon mold and cured it in an oven at 110° C. for 4 hrs. The cured PDMS mask layer was then peeled off from the mold to form a microfluidic flow-patterning layer. The layer was cut into multiple pieces, each hole-punched to create inlets and outlets for its channels in further use.

Subsequently, AuNR stock solution (0.2 nM) was centrifuged three times at 5700 rpm for 10 min, and the pellet was resuspended the pellet in deionized (D.I.) water to remove excessive CTAB in the solution. The AuNR solution was further diluted 8 times before the microarray fabrication. Glass slides (type) were first treated with Piranha solution ($H_2SO_4:H_2O_2=3:1$) for 10 min, rinsed thoroughly with D.I. water and kept in an ultrasonic bath with ethanol for 30 min. The surfaces of the glass substrates were treated under $O_2$ plasma for 2 min at 18 W (COVANCE 1-MP, Femto). This created a negatively charged glass surface owing to the dissociated hydroxyl groups existing on the glass, which enabled the glass substrate to attract the CTAB stabilized positively charged AuNRs onto its surface. Immediately after the surface treatment, one of the microfluidic flow-patterning PDMS mask layer pieces prepared above was bonded onto each glass substrate. Two µL of AuNR solution was loaded into each channel at a flow rate of 1 82 L/min and incubated overnight, which was followed by sealing of the inlets and outlets with a cover glass to prevent evaporation and avoid dry-out of the AuNR solution.

After the incubation, all the channels were washed with 100% ethanol to remove unbound AuNRs. This resulted in formation of AuNR microarray patterns on the regions of the glass surface covered by the channels. The SEM image showed that the resulting surface density of AuNRs on each microarray is around 1 particle per 2.56µm2.

Gold nanorod microarray functionalization. After constructing the AuNR microarray patterns on the glass substrate, they were functionalized within the microfluidic flow-patterning channels constructed above by forming a self-assembled monolayer (SAM) through simple ligand exchange (Eck, W. et al. ACS Nano 2, 2263-2272 (2008). A stock solution of thiolated alkane 10-Carboxy-1-decanethiol (HS-$(CH_2)10$-COOH) was diluted to 1 mM in 100% ethanol and flown through the patterning channel on the glass substrate. The strong binding of the thiol anchor group with the gold surface enabled the thiolated alkane to replace the CTAB coating and serve as a linker to probe antibodies. The antibody linking was performed by way of the antibody binding to the —COOH functional group through standard 1-ethyl-3-[3 -dimethylaminopropyl]carbodiimide/Nhydroxysuccinimide (EDC/NHS) coupling chemistry (Grabarek, Z. & Gergely, J. Anal. Biochem. 185, 131-135 (1990)) Briefly, a mixture of 0.4 M EDC (Thermo Scientific) and 0.1 M NHS (Thermo Scientific) were injected at a 1:1 volume ratio in 0.1 M MES(1-ethyl-3-[3-dimethylaminopropyl]carbodiimide hydrochloride, Thermo Scientific) solution through the microfluidic flow-patterning channels and activated the AuNRs microarray surfaces on the glass substrate. After the surface activation, primary cytokine antibodies (Ebioscience) were diluted from 100 to 10 µg/mL in 1× PBS, loaded into individual channels and incubated at room temperature for 60 min. This resulted in the construction of six meandering parallel AuNR stripe patterns of 25 µm in width and 2 cm in length at a pitch of 50 µm on the glass substrate, each functionalized with distinct antibody molecules. These patters formed the LSPR biosensor microarrays affording multiplex detection of 6 different cytokines. To suppress the non-specific binding on the detection surface, 10 µL of 1% BSA (Albumin, from bovine serum, SIGMA) in 1×PBS and 1× casein (5× Casein block solution, Surmodics BioFX) blocking buffer was added into the microfluidic flow-patterning channels and incubated for 20 min. During all the process steps, the reagent solutions were loaded using a syringe pump (LEGATO210, Kd Scientific) at 1µL/min. Between every step, the AuNR microarray surface was thoroughly washed to remove any excessive solutions or molecules using 20 µL of 1×PBS at 3 µL/min.

Optical setup and LSPR microarray imaging (LSPRmi) measurement. Following the AuNR microarray antibody functionalization process, the PDMS mask layer was removed from the glass substrate and immediately replaced with another PDMS layer with sample-flow microfluidic channel arrays. This new PDMS layer was fabricated following the same procedure as described for the construction of the PDMS microfluidic flow-patterning mask layer as described above. During the process of assembling the assay chip, the new PDMS layer was bonded onto the glass substrate such that the sample-flow channel arrays (200 µm (W)×2.5 cm (L)×50 µm (H)) were placed perpendicular to the LSPR microarray stripes. The constructed microarray assay chip was mounted on a motorized X-Y stage (ProScanIII, Prior Scientific, Rockland, Mass.), manually loaded a sample of ~5 µL to each of the on chip flow channels using a pipette, and performed automated image scanning at a rate of 180 sensing spots/min. FIG. 8 shows the system setup by which the AuNR microarray arrays were detected and imaged based on a dark-field LSPR imaging technique.

Figure 5:
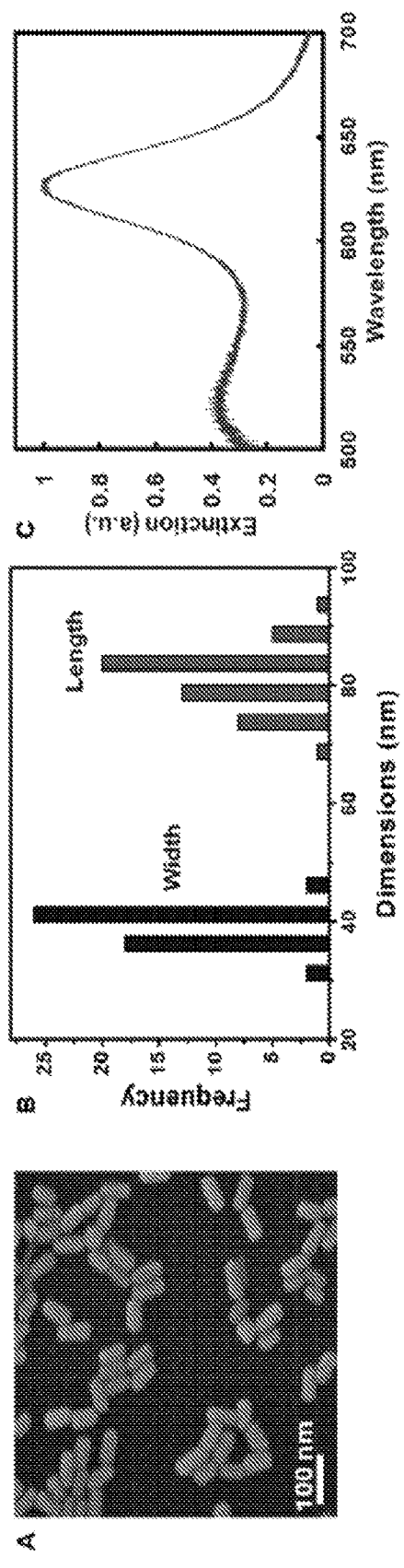
FIG. 5 shows (A) Scanning electron micrograph of AuNR drop cast onto a conductive glass substrate. (B) Statistics of the length and width of the AuNRs measured from high magnification electron microscopy in (A). (C) Extinction spectra of AuNRs in solution showing the resonant Rayleigh scattering wavelength at around 626 nm.

Briefly, the LSPR microarray imaging process started with guiding white illumination light into the dark-field condenser oil lens (n.a. 1.20 to 1.45, Mager Scientific) installed on the inverted fluorescent microscope (Nikon Eclipse Ti—S, Nikon). Binding of analyte molecules onto the nanostructured metal surface of each microarray induced an increase in the scattering rate of light within a certain spectral band as well as a red shift in the LSPR peak (630 nm for the AuNRs as shown in FIG. 5). A band pass filter (610-680 nm) was used to capture the maximum intensity increase observed for the microarrays during analyte surface binding. Images of microarrays were obtained with the EMCCD camera and recorded using NIS-Element BR analysis software. A customized Matlab program was used to analyze and quantify the scattering intensity shift for each microarray pattern. The region of interest was automatically selected through an edge detection/background subtraction algorithm, and then the raw data of each pixel was read out and processed.

Electromagnetic-field optical simulation on a single gold nanorod upon local refractive index change. In order to theoretically estimate the limit of detection of the LSPRmi measurement, a finite difference time domain (FDTD) simulation was performed and the scattering efficiency on a single AuNR was predicted using commercial multi-physics simulation software, COMSOL. The simulation used the dimensions of the AuNR that were determined by the results of the material characterization described above Information (40 nm in diameter, aspect ratio: 2). The plasmonically decoupled AuNR arrangement in the fabricated microarray patterns (FIG. 1) allowed one to focus attention to the LSPR behavior of the single AuNR, which significantly simplified the simulation. The frequency-dependent complex permittivity of gold was derived from Lorenze-Drude model (Kabashin, A. V. et al. *Nature Mater.* 8, 867-871 (2009)).

The far-field domain was defined as a spherical shell surrounding the AuNR with a radius identical with half the wavelength of incident light. As the boundary condition of the simulation, a perfectly matched layer of thickness identical with half the incident light wavelength was set on top of the surface of the far-field domain spherical shell, where the intensity of scattering light from the AuNR exponentially decays. The wave vector and electric field polarization of the incident light was set to be perpendicular and parallel to the orientation of the AuNR, respectively. This excited the longitudinal resonant mode of the AuNR in the simulation. The mesh size was set to be 1 nm on the AuNR surface and no larger than 1/10 of the studied wavelength elsewhere (FIG. 9A).

The spatial distribution of the electromagnetic field on the far-field plane was calculated at varying frequencies with and without the presence of the AuNR to determine the intensity of scattering wave from the AuNR, IAuNR, and the background signal intensity, Ibackgound. The scattering cross section Cscs of the AuNR is determined by integrating the intensity of scattering wave over the surface of the far-field plane $\Omega$ as $$C_{SCS} = \int \frac{I_{AuNR}}{I_{background}} d\Omega \quad (1)$$

and is also used for calculation of the limit of detection.

Next, a simulation was performed to predict how protein binding would enhance LSPR by mapping the spatial distribution of the normalized local electric field intensity ($|Ey|^2/|E0|^2$) near the surface of a bare AuNR (FIGS. 9B and 9C), where $|Ey|^2$ is the intensity of the y-component of the local field and $|E0|^2$ is the field intensity of the incident light. The spectral shift of light scattered from the AuNR due to protein binding was simulated. The simulation modeled protein binding as formation of a uniform dielectric layer on an antibody-functionalized AuNR surface, which was assumed to cause the near-surface refractive index value to change from 1.33 (water) to 1.5 (hydrated protein) (Voros, J. *Biophys. J.* 87, 553-561 (2004)). The protein attached to the AuNR surface can be either the analyte or the probe antibody used in the study. The simulation was performed with the thickness of the protein layer ranging from 0 to 10 nm with a 2 nm increment. Comparing FIG. 9B and FIG. 9C, it is shown that coating the AuNR with a 10 nm-thick protein layer is predicted to yield a notable enhancement of $|Ey|^2/|E0|^2$. FIG. 9D shows a set of the scattering light spectra of the AuNR coated with the protein layer of varying thickness.

Theoretical prediction of the detection limit of the LSPRmi measurement. The simulation described above predicts a noticeable spectral red-shift as well as an intensity enhancement for scattering light from the AuNR at a larger protein coating thickness. (FIG. 9D) Here, the scattering light intensity is the LSPR signal that is directly observed in the measurements. Using the simulation approach above, the quantitative values of the spectral shift and intensity variation of the LSPR signal induced by analyte binding on a single AuNR were calculated. The antibody conjugation of the AuNR in the assay was assumed to form a uniform layer of closely packed antibody molecules with a thickness of 7 nm (Erickson et al., Biol. Proced. Online. 15, 32-51 (2009)) and a refractive index of 1.5. Furthermore, a theoretical volume called the "sensing volume" on top of the antibody layer was assumed (inset of FIG. 10). The thickness of the sensing volume is equivalent to the effective diameter of the analyte molecule (typically 3.4 nm for cytokines; Erickson et al., Biol. Proced. Online. 15, 32-51 (2009)). In the model, the refractive index of the sensing volume layer was also set to be 1.5 when the volume was fully occupied by the analyte molecules. The LSPR signal variation $\Delta I$ due to surface binding of a single analyte molecule is then given by:

$$\Delta I = \frac{\Delta S}{V_s} * \Delta RI * V_a \quad (2)$$

where $\Delta RI$ is the refractive index change in the volume of the sensing volume Vs, which was described above, Va is the volume of the single analyte molecule, and $\Delta S$ is the experimentally observed signal difference between before and after loading the analyte molecules onto the AuNR surface. More specifically, $\Delta S$ is the analyte adsorption induced LSPR peak wavelength shift, given by $$\Delta S = \frac{\Delta \lambda_p}{RIU}$$

for spectrum-shift measurement, where $\Delta \lambda_p$ is the resonance peak shift, and RIU is the refractive index unit (=1). $\Delta S$ is the analyte adsorption-induced LSPR intensity (e.g., scattering intensity) shift, given by $$\Delta S = \frac{\int_{610}^{680} \Delta C_{SCS} d\lambda}{RIU}$$

for the intensity-based imaging measurement, where $\int_{610}^{680} \Delta C_{scs} d\lambda$ is the integration of the change in the scattering cross section $\Delta C_{scs}$ after the analyte loading over $\lambda$=610-680 nm, which is the optical filter band used in this study (grey area in FIG. 9D). Here, $\Delta C_{scs}$ is derived from Eq. (1) above. For a given analyte concentration of [A] in the flow channel, the probability of the analyte binding event on the single AuNR surface $\theta$ can be estimated using Hill-Langmuir isotherm as (De Boer, J. H. The dynamical character of adsorption, second ed. (Oxford University Press, London, 1968)):

$$\theta = \frac{[A]^n}{K_d + [A]^n} = \frac{1}{1 + \left(\frac{K_A}{[A]}\right)^n} \quad (3)$$

where Kd is the binding constant determined at the equilibrium dissociation state between the antibody and its engaging antigen, KA is the ligand concentration producing half occupation, and n is the Hill coefficient. Alternatively, θ represents the ratio of the number of occupied binding sites over the total number of sites available for analyte binding.

Assuming the AuNR deposition density per unit area within the detection channel to be D and the total binding sites on one single AuNR to be $N_s$, the overall signal intensity change $\Delta I_A$ collected from the microarray sensing area can be calculated by:

$$\Delta I_A = \frac{\Delta I}{D} * D * N_s * \left(\frac{1}{1 + \left(\frac{K_A}{[A]}\right)^n}\right) \quad (4)$$

The LOD of the analyte for LSPRmi can then be determined when the signal change equals to the system signal uncertainty $U = \sqrt{U_{sys}^2 + U_{fit}^2}$, where $U_{sys}$ is the uncertainty due to the detection system and $U_{fit}$ is the uncertainty due to the peak fitting when gathering the scattering spectrum. Therefore, one obtains:

$$U = \Delta I * N_s * \left(\frac{1}{1 + \left(\frac{K_A}{[A]}\right)^n}\right) \quad (5)$$

Combining Eq. (2) and (5) allows one to analytically estimate the LOD of LSPRmi as:

$$LOD[A] = K_A * \left(\frac{\frac{S(r)}{V_s} * \Delta RI * V_a * N_s}{\sqrt{U_{sys}^2 + U_{fit}^2}} - 1\right)^{-1/n} \quad (6)$$

Figure 10:
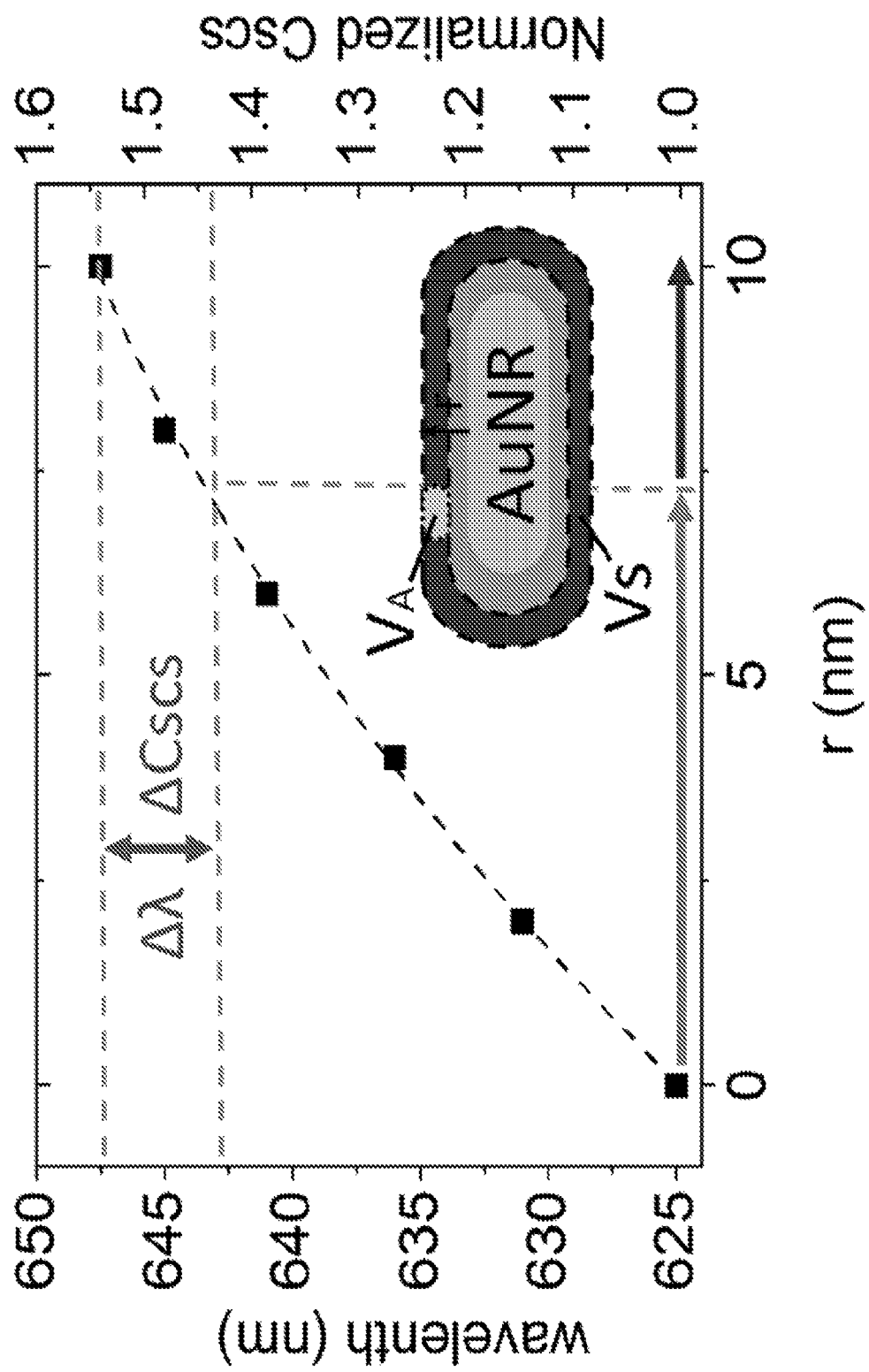
FIG. 10 shows calculated scattering spectrum peak wavelength (alternatively, scattering cross section normalized by the value for a bare AuNR surface) as a function of the thickness of protein layer covering the AuNR surface, r.

To estimate the sensitivity improvement of the LSPRmi over the conventional spectrum-based LSPR measurement, the signal-to-noise ratio upon an analyte binding event is quantitated using first order Langmuir equation in Eq. (6). The total available binding sites on one single AuNR (40 nm(W)×80 nm (L)) can be calculated to be ~361. In an extreme case where AuNR surface is fully occupied, the spectrum shift (Δλ=5.1 nm) and scattering cross section change integrated from 610 nm to 680 nm (ΔCscs=7.2%) as shown in FIG. 10.

According to the most recent study using a spectrum-based nanorod LSPR biosensor (Nusz et al., ACS Nano 3, 795-806 (2009)), the researchers' experimental setup (incandescent white light source, CCD detection of scattering) yielded a signal variance of $U_{spectmm}$=0.3 nm. The uncertainty due to the sensor and signal processing unit in the system is $U_{intensity}$=0.11% by measuring blank samples. Substituting these numbers into Eq. (6) allows one to calculate the ratio of the LOD of the intensity-based LSPRmi platform, $LOD_{intensity}$, to that of the conventional spectrum-shift measurement technique, $LOD_{spectrum}$, as $$\frac{LOD_{intensity}}{LOD_{spectrum}} = \left[\left(\frac{\Delta I_{spectrum} * N_i}{U_{spectrum}} - 1\right) \Big/ \left(\frac{\Delta I_{intensity} * N_i}{U_{intensity}} - 1\right)\right] = \sim \frac{1}{10} \quad (7)$$

Thus, it is estimated that the technique reduces the LOD by a factor of ~10 as compared to the conventional LSPR detection scheme.

Figure 11:
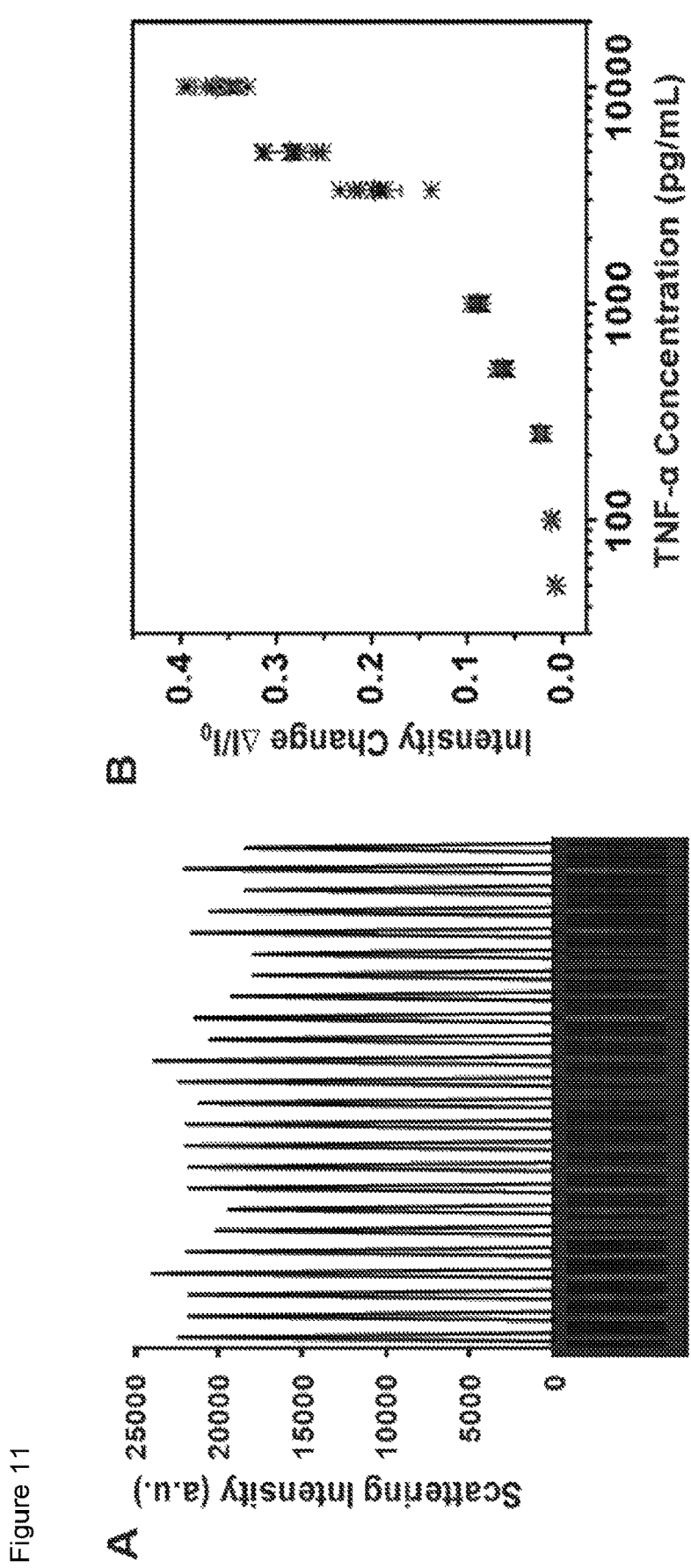
FIG. 11 shows (A) Line intensity profile of the uniformly fabricated AuNR microarrays, which was measured using dark-field imaging microscopy. (B) Calibration plots showing the LSPRmi signal variation with recombinant TNF-α concentration, where each star represents an individual measurement data point.

AuNR microarray intensity and LSPRmi signal variance. The structural variance across the AuNR microarrays deposited on a common glass substrate from scanned dark-field images taken for their calibration measurements were characterized (FIG. 11A). The upper panel in FIG. 11A shows the line intensity profile of 24 consecutive AuNR microarrays on the same chip. The image data indicate an average intensity of ~21,000 with a coefficient of variance (CV) around 8% across all the microarrays. It reveals the consistency of the fabrication technique in producing microarray stripes with good array-to-array structural uniformity. Such uniformity provided a CV of ~7% or lower across calibration data points taken for 10 microarray stripes on the same chip at a given analyte (TNF-α) concentration (FIG. 11B). The result verified the high reproducibility and accuracy of the LSPRmi measurements using these microarrays.

System uncertainty and limit of detection of LSPRmi. In order to characterize the uncertainty and limit of detection of the LSPRmi system, a control experiment measuring the variance of the background signal with antibody-conjugated AuNR microarrays with no cytokines loaded was performed. The average system uncertainty was calculated to be ~0.11%, which was determined by the minimum distinguishable signal equivalent to a confidence factor set to be 3 times the standard deviation of the background noise (σ). The detection limits of the target cytokines were thus obtained from 3 σ/$k_{slope}$, where $k_{slope}$ is the slope of the regression of the calibration curves using sigmoidal curve-fitting.

Results

Figure 6:
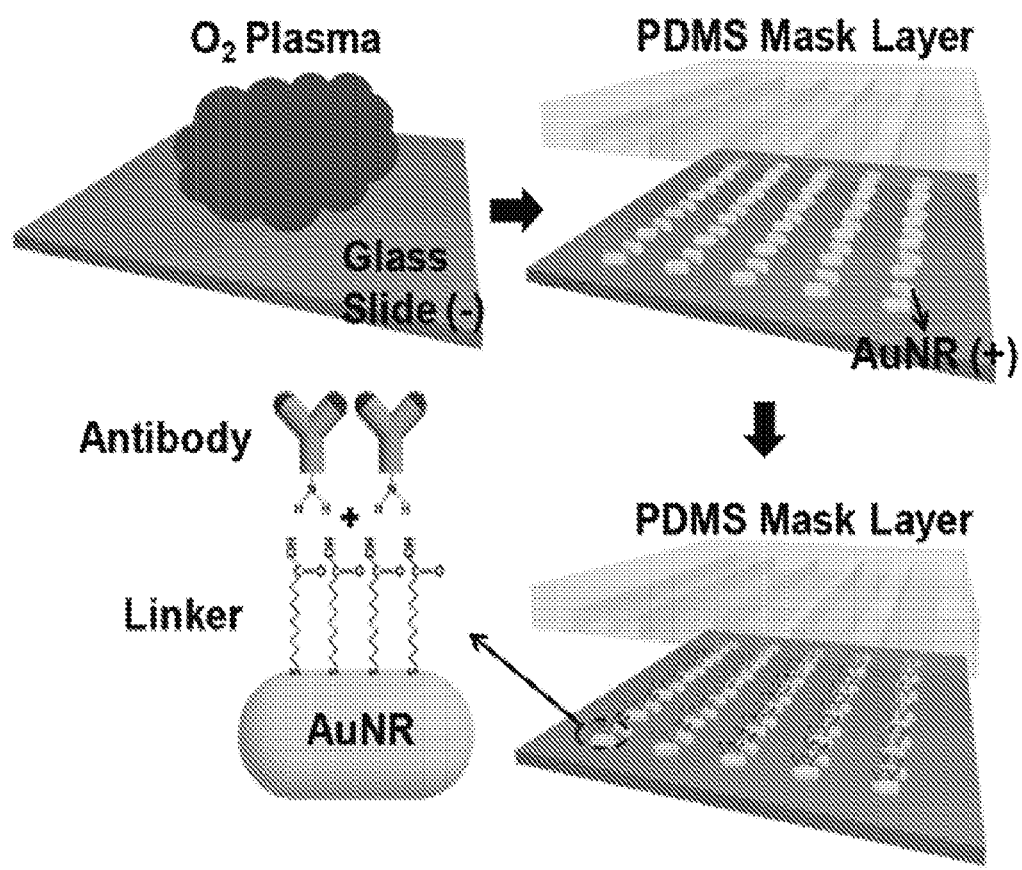
FIG. 6 shows a schematic of the LSPRmi chip patterning process that entails glass pre-treating, AuNR deposition, and antibody function.

LSPR microarray chip preparation. The LSPRmi biochip includes eight parallel microfluidic channels of 250 nL in volume and six meandering stripes of antibody-functionalized AuNR (characteristic properties of the AuNRs are shown in FIG. 5) ensembles with ten turns on a glass substrate, which run orthogonal to the channels (FIG. 1a). Each microfluidic channel has inlet and outlet ports for reagent loading and washing. This chip design gives rise to an array of 480 stripe shaped LSPR biosensing spots of 25μm wide and 200 μm long each on the entire chip. The AuNR stripes were conjugated with antibodies against six different cytokines: interleukin-2 (IL-2); interleukin-4 (IL-4); interleukin-6 (IL-6); interleukin-10 (IL-10); interferon-gamma (IFN-γ); and tumor-necrosis-factor alpha (TNF-α) using a one-step microfluidic patterning technique (FIG. 6). The microfluidic patterning technique allowed for construction of ten segments of six collocating parallel multiplex immunoassay spots in each channel without cumbersome manual reagent dispensation on the large number of locations (FIG. 1a).

Figure 2:
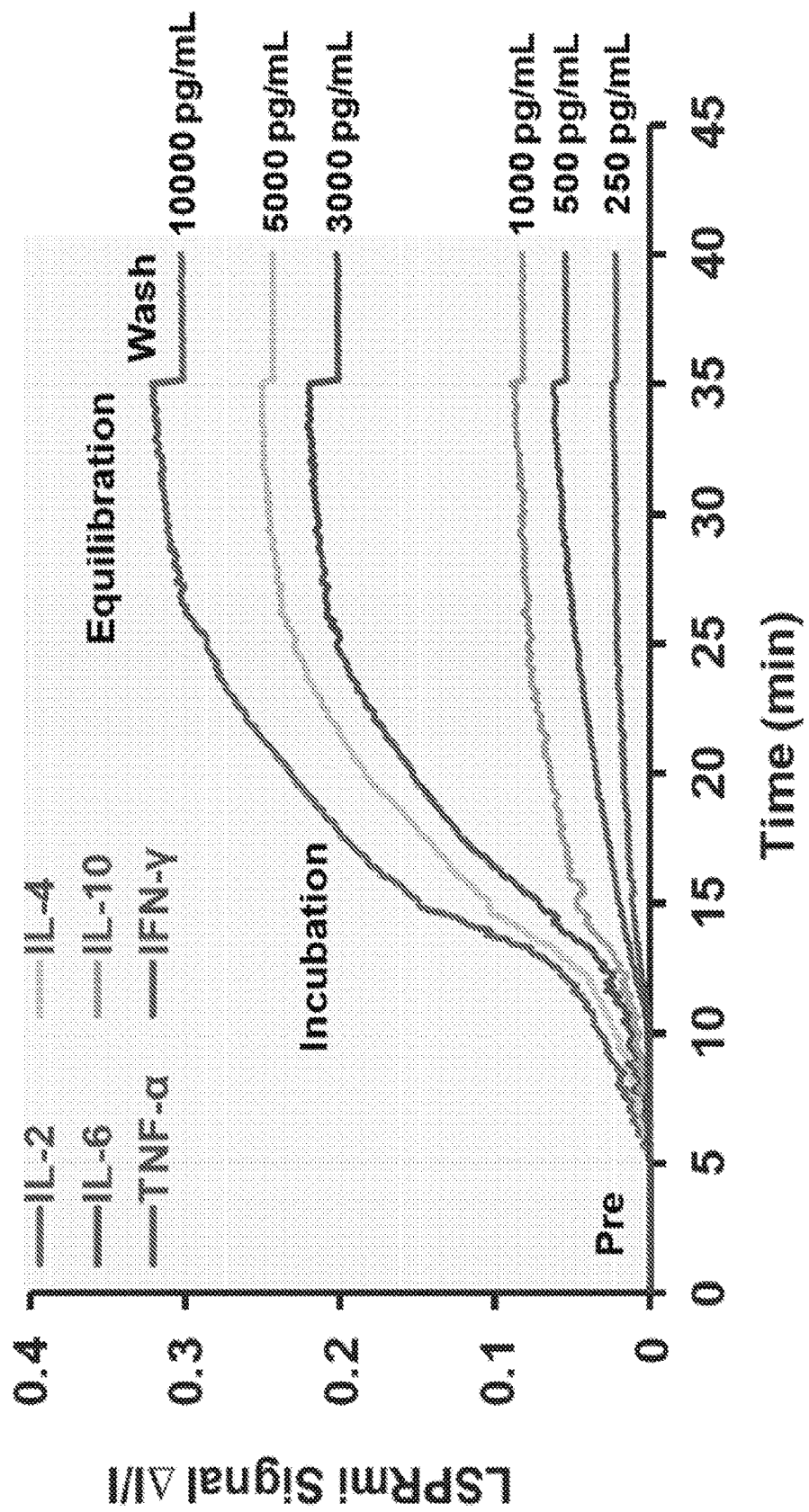
FIG. 2 shows real-time AuNR microarray signals during multiplex cytokine detection.
Figure 7:
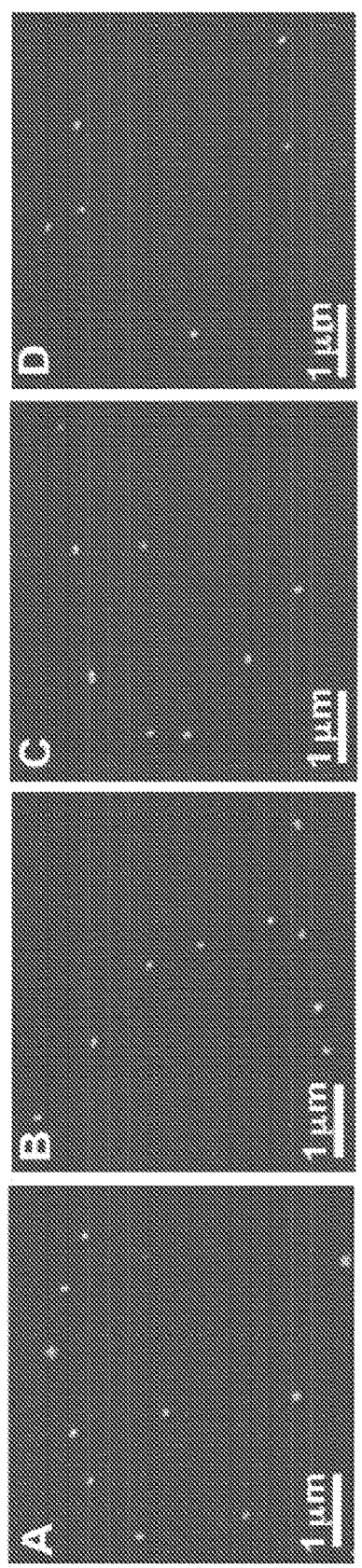
FIG. 7 shows scanning electron microscope images of AuNR particles within a microarray pattern on a glass substrate.

The scanning electron microscopy images show that the LSPR sensing spots are coated with a disordered monolayer at a surface number density of ~1 particles per 2.56 um2 (FIG. 1a and FIG. 7), which corresponds to an average particle-to-particle distance >200 nm (FIG. 1b). The theoretical calculation predicts a much shorter (65 nm) decay length of the highly localized photo-excited EM field surrounding each nanoparticle (Inserted panel of FIG. 1b). The disperse distribution of the nanoparticles eliminates complicated electromagnetic couplings between neighboring nanoparticles in the ensembles. This critically makes the multi-arrayed LSPR sensor performance uninfluenced by the disordered nanoparticle arrangement. The ensemble of ~2,000 plasmonically uncoupled AuNRs on each sensor spot yields a scattering spectrum with a distinct resonance (FIG. 1c). Thus, the principle of the LSPRmi platform relies on the scattering light intensity change in a particular plasma resonance range caused by the target analyte binding onto the AuNR Real-time LSPR multiplex immunoassay. Characterizing the dynamic performance of the LSPR biosensors allows one to assess the total assay time. To this end, the real-time sensor signal variations associated with analyte surface binding were measured in the multiplex scheme. This measurement used a mixture of the six target cytokines suspended in phosphate buffered saline (PBS) solution. Here, a different concentration level was set for each analyte such that IL-2, IL-4, IL-6, IL-10, TNF-α, and IFNγ were at 10,000 pg/mL, 5,000 pg/mL, 3,000 pg/mL, 1000 pg/mL, 500 pg/mL and 250 pg/mL, respectively. The cytokine mixture was loaded into one of the microfluidic channels of the device and the time-course signal variation from the sensor spots (FIG. 2) was observed. From this measurement, it was found that the analyte-binding event reached the equilibrium within 30 min after the introduction of the cytokine mixture. This rapid analyte binding kinetics allows the assay to be performed with a very short incubation time as compared to conventional fluorescence sandwich immunoassays. After the equilibrium was reached, the loaded samples were washed to remove non-specifically bound serum constituents from the sensor surfaces. This resulted in a sensor signal intensity reduction by ~8%.

High-throughput LSPR microarray biosensing and calibration. A significant feature of LSPRmi chip assay is its ability to analyze the multiple analytes at high throughput. This capability was demonstrated by performing massively parallel data-intensive sensor calibration using the device within a short period of time. The obtained calibration data for each analyte subsequently allowed for a determination of the dynamic range and detection limit of the assay. At first, eight PBS samples were prepared, each containing a mixture of the six purified cytokine species (i.e., IL-2, IL-4, IL-6, IL-10, IFN-γ, and TNF-α) and they were manually pipetted into the inlets of the eight channels of the device (FIG. 3a). Each sample introduced to one of the channels contained the cytokines all at the same concentration, which was one of the eight levels between 50 to 10,000 pg/mL. The sensor response was recorded over 480 individual AuNR microarray sensing spots on a single chip at a scanning rate of 180 spots/min before sample loading and after washing when the analyte surface binding reached equilibrium at ~30 min. Thus the total assay time including sample loading and washing (5 min), incubation and equilibration (30 min), and image scanning (5 min) was around 40 min. FIG. 3b shows a result of mapping the local intensity variation ($\Delta I/I_0$) after loading and washing cytokine molecules over 480 sensor spots, where I0 is the original sensor signal intensity prior to the assay and $\Delta I$ is the intensity shift after the assay. Sensor calibration curves were then obtained for the six cytokines by plotting the normalized intensity shift $\Delta I/I0$ spatially averaged over 10 sensor spots as a function of analyte concentration (FIG. 3c). It was additionally verified that these measurements were consistent across ten sensor spot replicates with an averaged coefficient of variance around 7% as described above. The calibration curves indicate that the assay achieves a large dynamic range from 10 to 10,000 pg/mL for the cytokine biomarkers. The dashed lines in the plots represent sigmoidal curves fitted to data points (Hill type). The limit of detection (LOD) was determined for each analyte as defined by $3\sigma/kslope$, where $\sigma$ and kslope are the standard deviation of background signal obtained from blank control and the slope of the regression of each calibration curve, respectively. The determined LOD's were 11.43 pg/mL (TNF-α), 6.46 pg/mL (IFN-γ), (IL-2), 20.56 pg/mL (IL-4), 11.29 pg/mL (IL-6), and 10.97 pg/mL (IL-10) as summarized in Table 1.

Figure 4:
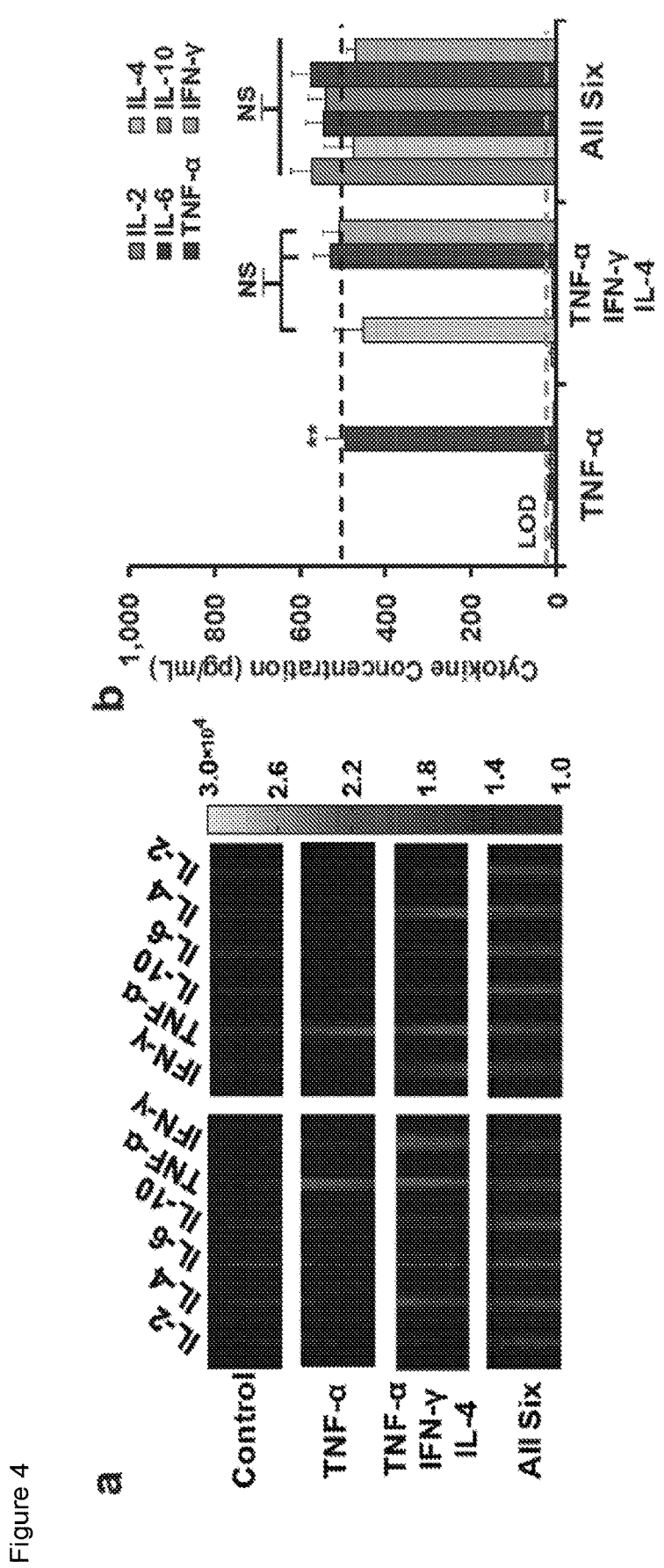
FIG. 4 shows multiplex cytokine detection in healthy donor serum matrix and patient serum samples. (A) Dark-field images of AuNR microarrays within a single microfluidic detection channel loaded with different sample mixtures of recombinant cytokines spiked in serum matrix. (B) Cytokine concentrations quantified for the samples in (A). (C) Correlation between data obtained from the LSPRMi assay and gold standard ELISA for the spiked-in serum samples with cytokine concentrations ranging from 32-5000 pg/mL. d) Five-day cytokine concentration variations measured by the LSPRmi assay for serum samples extracted from two post-CPB-surgery pediatric patients.
Figure 4:
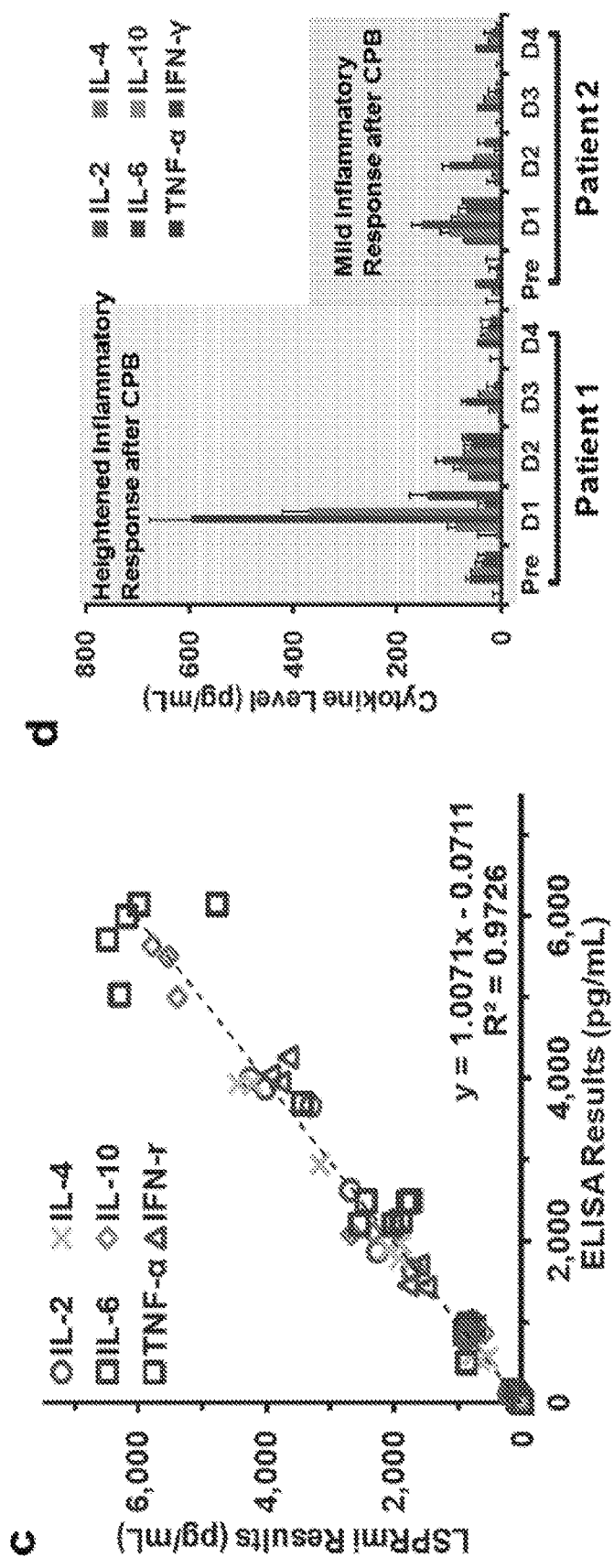

Multiplex LSPR microarray immunoassay of serum cytokines. To test the multiplex immunoassay capability of the device, sets of serum samples were prepared using heat inactivated and charcoal absorbed human serum and spiked with different mixtures of cytokines. Using these samples, post-assay signal images were obtained for the panel of the six striped sensing spots integrated within the same microfluidic channel, where a sample of particular cytokine mixture pattern was loaded. It was observed that the signal intensity of each sensor array was dependent on the target cytokine and independent of the presence of off-target cytokines in the serum solution (FIG. 4a). The intensity shift was translated into the analyte concentration detected at each sensor from the calibration curves obtained above (FIG. 4b). No statistically significant difference was found between the measured cytokine concentrations and the expected value of 500 pg/mL. Furthermore, the sensors targeting cytokines absent from the serum matrix yielded signals below their LOD as expected. The percent recovery, which is defined to be the amount of analyte detected as the fraction of the amount of known analyte in a sample, was calculated. The percent recovery for all cytokines fell within an acceptable range of 85-115% (Guidance for Industry: Bioanalytical Method Validation. Rockville, Md.: Food and Drug Administration, U.S. Department of Health and Human Services, 2001). Thus, the multiplex assay exhibits minimum cross-reactivity amongst the six cytokines biosensors.

Assay validation with the gold standard method. Wide acceptance of a new multiplex immunoassay method utilizes its full validation with the existing "gold-standard" assay—ELISA. Healthy-donor serum samples spiked with a mixture of six cytokines at concentrations ranging across the entire dynamic range of the assay were prepared and used to perform multiplex immunoassay using the LSPRmi chip. Together with this assay, ELISA-based measurements of the analytes for the same samples as above were performed. The ELISA-based measurements were based on the singleplex scheme. In other words, the assay targeted only one of the six cytokines in each measurement to avoid any potential crosstalk between different probe molecules. The singleplex ELISA measurements were repeated for all the six cytokines across the serum samples prepared above. Finally, the LSPRmi immunoassay measurements were compared with the ELISA measurements and an excellent correlation ($R2=0.9726$) was observed, resulting in a nearly one-to-one linear regression between the both assay methods (FIG. 4c).

Immune status monitoring of pediatric patients with cardiopulmonary bypass surgery. Leveraging the strengths of the LSPRmi immunoassay, the utility of the technology to allow monitoring of the inflammatory response of neonates following cardiothoracic surgery necessitating cardiopulmonary bypass (CPB) was demonstrated. Repair of congenital heart defects necessitates open heart surgery using CPB to supplant heart-lung function during surgery, and is the most common birth defect in the United States (Agus, M. S. D., et al. N. Engl. J. Med. 367, 1208-19 (2012)). Blood contact with the artificial surfaces of the CPB circuit is known to elicit a substantial inflammatory response in the immediate post-operative period that is normally restored to pre-operative levels within 48 hours (Mahle, W. T., et al. Ann. Thorac. Surg. 97, 950-6 (2014)). Serum samples were collected prior to surgery (Pre), and on post-operative days one (D1), two (D2), three (D3), and four (D4) and the LSPRmi immunoassay was used to quantify circulating serum cytokine levels on these days in two neonates undergoing congenital heart surgery with CPB (FIG. 4d). Increased levels of both IL-6 and IL-10 were observed on post-operative day one following CPB in both patients, followed by a return to pre-operative levels of all cytokines on postoperative days D2, D3, and D4. The LSPRmi assay demonstrates a capacity of detecting variable degrees of cytokine expression.

TABLE 1

The LOD's of target cytokines were determined from the minimum distinguishable analytical signal defined by $3\sigma/k_{slope}$, where $\sigma$ is the standard derivation of the LSPRmi signals from blank samples, and kslope is the regression slope obtained from the calibration curves using sigmoidal curve-fitting.

| Cytokine | Blank S.D. ($\sigma$) (%) | $U_{system}$ ($3\sigma$) (%) | $k_{slope}$ (%)*(pg/mL)$^{-1}$ | LOD = $3\sigma/k_{slope}$ (pg/mL) |
|---|---|---|---|---|
| IFN-γ | 0.022 | 0.065 | 0.010 | 6.46 |
| TNF-α | 0.034 | 0.103 | 0.009 | 11.43 |
| IL-2 | 0.069 | 0.206 | 0.010 | 20.56 |
| IL-4 | 0.031 | 0.092 | 0.020 | 4.60 |
| IL-6 | 0.038 | 0.113 | 0.010 | 11.29 |
| IL-10 | 0.030 | 0.088 | 0.008 | 10.97 |

Example 2

Figure 12:
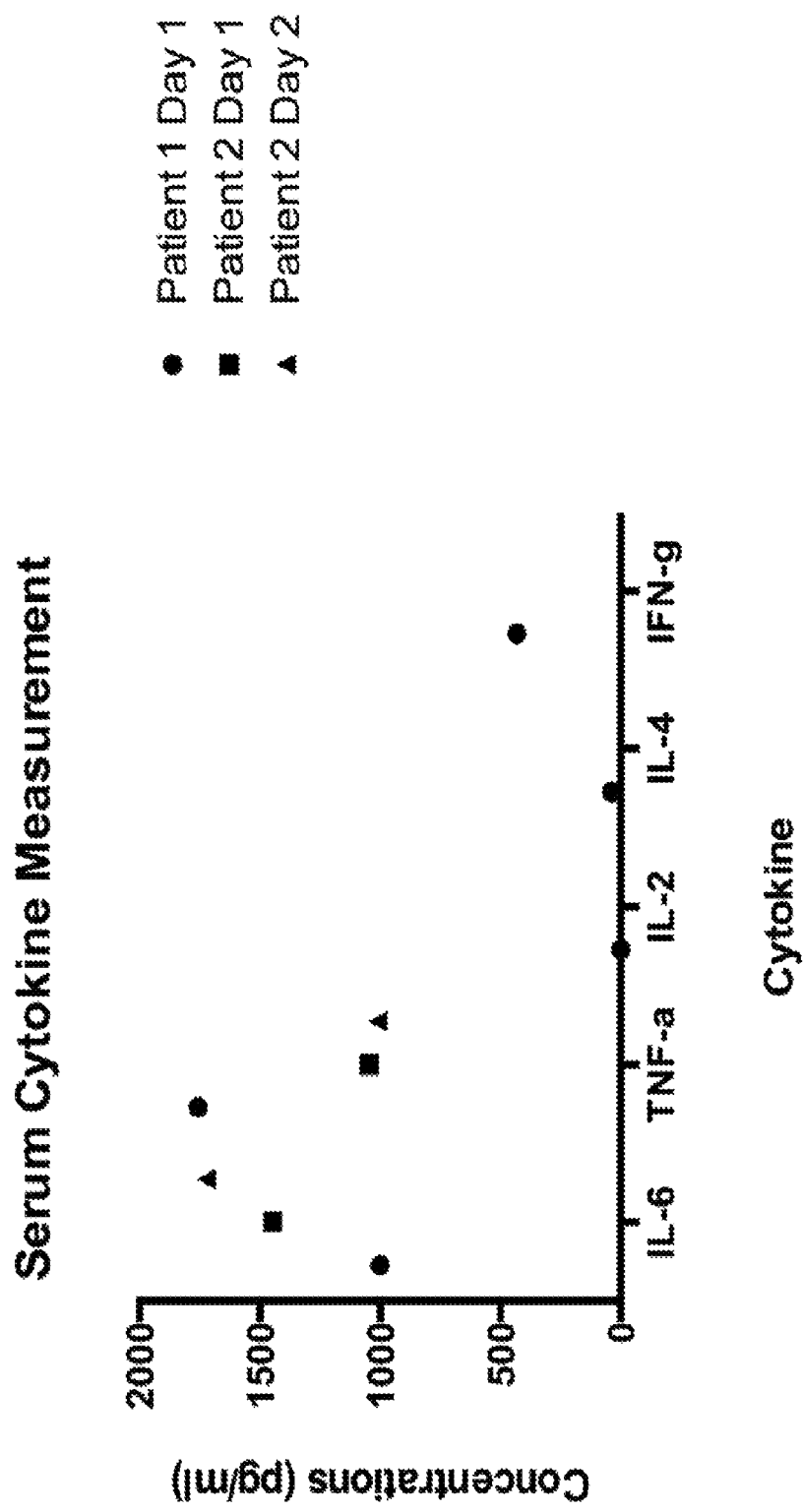
FIG. 12 shows cytokine levels in serum of leukemia patients.

The LSPR cytokine assay described in Example 1 was used to determine cytokine levels in leukemia patients undergoing treatment. Results are shown in FIG. 12. The two patients were patients with relapsed acute lymphoblastic leukemia (ALL) who had under gone chimeric antigen receptor T-cell therapy (CAR T-cell). This therapy results in the release of inflammatory mediators (cytokines) that result in a systemic inflammatory response syndrome leading to hemodynamic instability and shock. Two therapies are available to block the action of two of these cytokines; etanercept blocks tissue necrosis factor-alpha (TNF-a) and tocilizumab blocks interleukin 6 (IL-6). These therapies work if cytokine levels are elevated and over use of the therapies have the potential to immune suppress the patient putting them at risk for development of sepsis (overwhelming infection). Currently, the standard turnaround time for measuring cytokines is days so patients are typically treated without knowing cytokine levels.

Both of these patients presented to the PICU with the systemic inflammatory response syndrome that progressed to shock. The measurements were provided to the treating clinicians on patient 1 to help guide the tocilizumab therapy. No clinical decisions were made on the data from patient 2 due to the patient's clinical condition.

Example 3

This example describes AC electroosmosis (ACEO) incorporation into exemplary devices.

Fabrication & Functionalization

Figure 14:
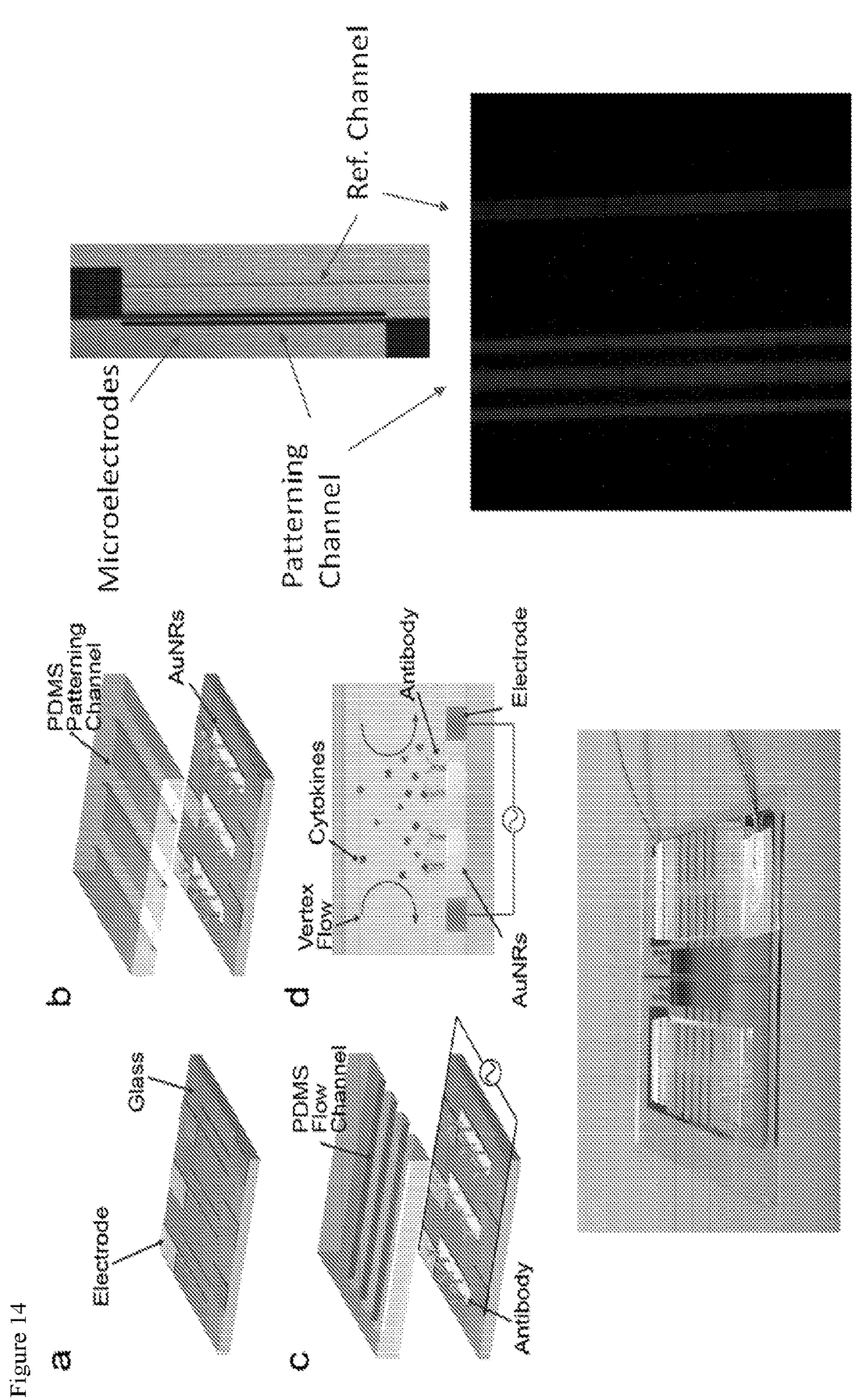
FIG. 14 shows (a) Deposition of microelectrodes (b) Surface functionalization of AuNR microarrays (c) Analyte sample loading using PDMS flow channel (d) Real-time detection of target analytes under ACEO vortex flow (e) Picture of an exemplary ACEO device (f) Dark field image of AuNRs barcode coupled with electrodes.

Device Fabrication:

The standard photolithographic liftoff, bulk micromachining and sputtering processes are utilized to deposit parallel coplanar Cr/Pt (50 nm) plate microelectrodes on glass substrates, as shown in FIG. 14a. Briefly, the glass wafers was treated with Piranha solution
(($HOSO_4:H_2O_2$=3:1 v/v), rinsed thoroughly with D.I. water and air dried before use. The electrode pattern was first transferred onto a pre-coated positive resist layer (AZ726) using a darkfield photomask and contact lithography. After removing the exposed photoresist with developer, an E-beam evaporation method (EnerJet Evaporator) was used to deposit a 10 nm of chrome as adhesion layer and then 50-nm of platinum on top of it. The electrodes coated glass substrates was soaked in pure acetone solution to remove the photoresist residue and grease, and then treated with nitric acid solution ($HNO_3:H_2O$=1:2 v/v), thoroughly rinsed with D.I. water, kept in ultrasonic bath with D.I. water, and air dried for further surface function.

Device Functionalization:

The surfaces of the glass substrates and the PDMS microfluidic mask layer were treated with $O_2$ plasma. Immediately after plasma treating, the PDMS mask and the electrodes on the glass substrate were aligned under a microscope to ensure that the PDMS patterning channels fall in between the adjacent electrodes (FIG. 2b). $O_2$ plasma treating can generate a negatively charged glass surface owing to the dissociated hydroxyl groups existing on the glass, which enables the glass substrate to attract the positively charged, CTAB stabilized AuNRs onto its surface. A colloidal solution containing AuNRs was loaded through the microfluidic patterning channel at a flow rate of 1.5 μl/min for 2 min in both direction. The chip was then stored in a petri dish for 2 hours with inlets and outlets sealed by a cover glass to prevent evaporation and avoid dry-out of the AuNR solution in the channels.

The microfluidic channels was then washed with DI water (around 5-6 μl) to remove the unbounded AuNRs in the solution and loaded with 1 mM Biotin PEG (polyethylene glycol, 10 kDa) Thiol water solution (NANOCS). The stronger affinity of the thiol anchor group with the gold surface enables the thiolated PEG Biotin to replace the CTAB coating and serve as a linker to probe streptavidin.

The PEG-Biotin functionalized AuNRs was incubated overnight with wet tissues in the Petri dish to construct a moisture environment and avoid dry-out.

Biosensing Platform

General sensing set up

Figure 15:
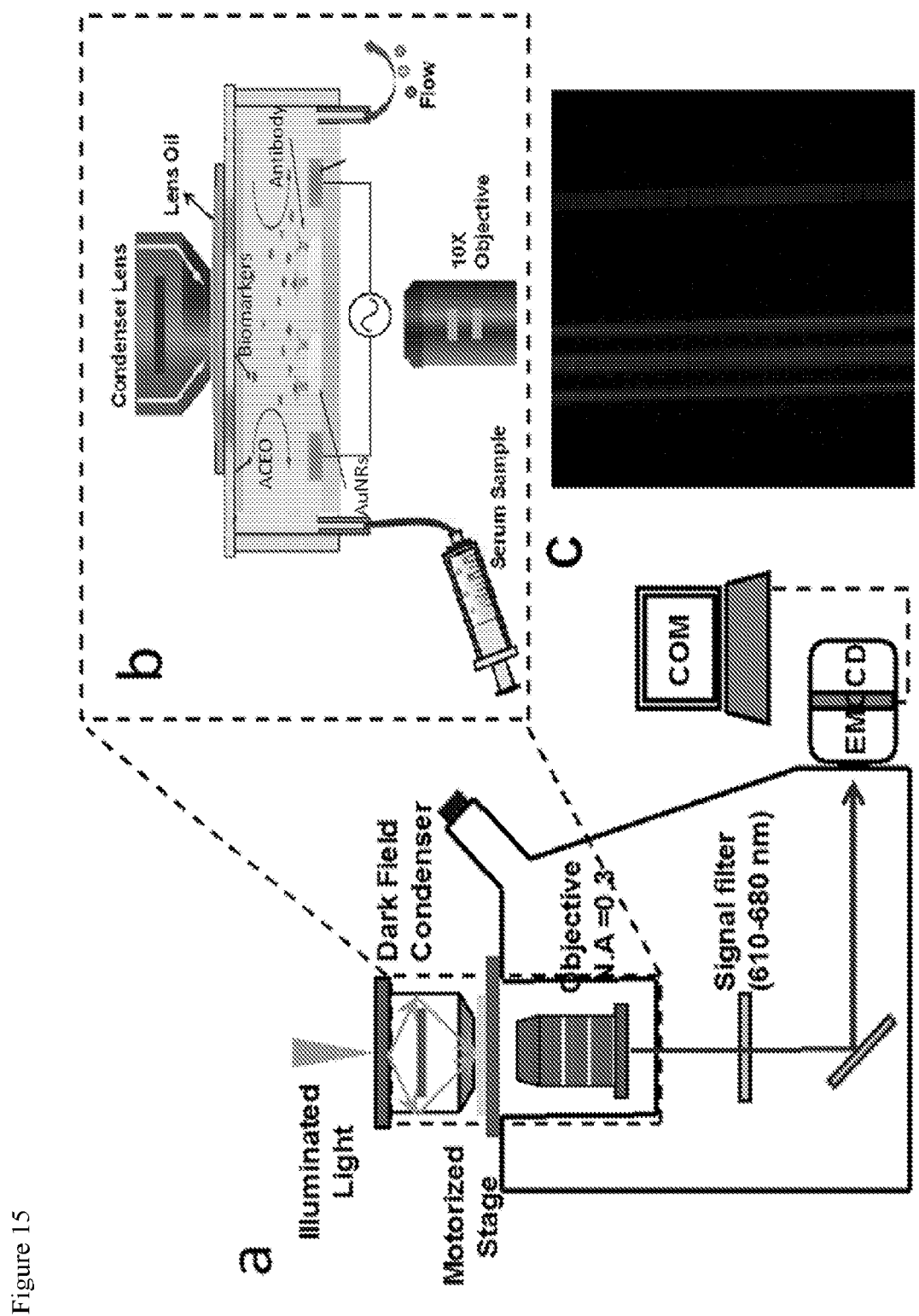
FIG. 15 shows (a) Schematic of the dark-field microscope setup (b) Surface reaction inside an exemplary ACEO coupled nanobiosensor (c) Real-time dark-field image collected by EMCCD.

Dark-field microscopy with an electron multiplying charge coupled device (EMCCD) was used in the signal detection for the ACEO coupled LSPR nanobiosensor described above, as shown in FIG. 15a. The LSPR-based detection measures the absorbance spectrum shift (local refractive index change) of a nanostructured metal surface due to the binding of analyte molecules. Here, this spectrum shift signal is converted into optical intensity change by using a proper band-pass filter (680/13) coupled with EMCCD detector. The optical intensity signal is analyzed across a large number of nanoparticle biosensors in the micro-array, which contains statistically and biologically meaningful information. The theoretical model predicts that this approach result in a LOD value more than 10 times lower than that of spectrum-shift detection schemes commonly used in conventional label-free LSPR biosensing.

Assay detail

The PDMS mask with loading channel was peeled off and immediately replaced with parallel straight channels (400 μm (W)×2.5 cm (L)×50 μm (H)) perpendicular to the electrode barcode, shown in FIG. 14c. To generate a proper ions concentration environment, 1000-time diluted×1 PBS solution was used as rinsing buffer to wash away the unbounded Biotin PEG Thiol molecules. The chip was then mounted on a motorized X-Y darkfield microscope stage (ProScanIII, Prior Scientific, Rockland, Mass.) with electrodes connected to two AC function generator (180 phase difference) and ready for measurements. Streptavidin was dissolved in 1000-time diluted×1 PBS with concentration range from 50 fg/ml (0.67 fM) to 100 pg/ml (1.33 pM) and was injected by syringe pump at a flow rate of 2 μl/min. The AuNRs microarray was detected and imaged based on darkfield LSPR imaging technique mentioned above. A band-pass filter (680/13 nm) was used to capture the maximum intensity increase of the microarrays due to Biotin-streptavidin binding on gold surface. The microarray image was real-time recorded by EMCCD camera using NIS-Element BR analysis software and was analyzed and quantified the scattering intensity change by a customized MATLAB code developed in our lab.

Results

Figure 16:
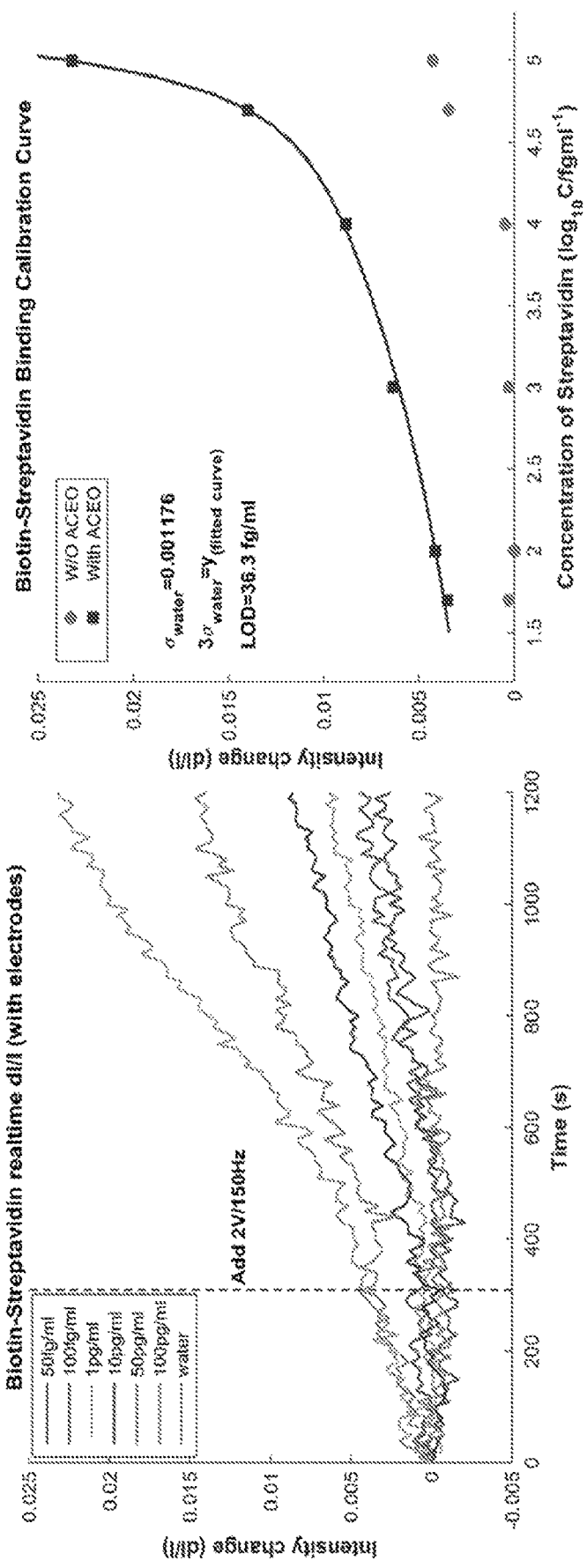
FIG. 16 shows (a) Real-time binding curve of biotin-streptavidin under different concentration (b) Calibration curve (c) Schematic of surface function (d) Test of non-specific binding.

Results show that the ACEO coupled LSPR nanobiosensor detected streptavidin down to 50 fg/ml (≈0.67 fM), as indicated in FIG. 16a. The limit of detection (LOD) for ACEO coupled biosensor is calculated to be 36.3 fg/ml (based on 3σ of the control signal, where σ is the standard derivation of signal when measuring the blank sample) which is approximately 1000 times lower than the LOD of that without ACEO (29.4 pg/ml), shown in FIG. 16b. Moreover, the assay time was shortened to 15 min twice as fast as previous assay with the same sample volume (5 μl). The shear-flow on sensing surface can also help eliminate non-specific binding, as shown in FIG. 16d.

Example 4

Early attempts to target cytokines, a key biologic component of the inflammatory response, in sepsis resulted in mixed results for more than 100 phase II/III clinical trials. The varied results from these studies are a direct result of the heterogeneous nature of this complex patient population, fundamental differences in genetics, as well as diverse disease etiologies (bacterial/viral infections, trauma) resulting in disparate classes of immune dysregulation. It was contemplated that integration of prospective biomarker risk-stratification and precision targeted anti-cytokine therapies in clinical trial design will greatly increase the likely-hood of the ability of these trials to show significant benefit.

The present example tests a validated biomarker risk-stratification algorithm and precision targeted anti-cytokine therapy using currently FDA-approved anti-cytokine biologics in clinical trial design.

Design/Methods: Briefly, the microfluidic immunoassay platform described herein that enables rapid (<30 min), multiplex cytokine (>6 analytes) quantification from small blood volumes (<1 drop of blood) was used.

Figure 17:
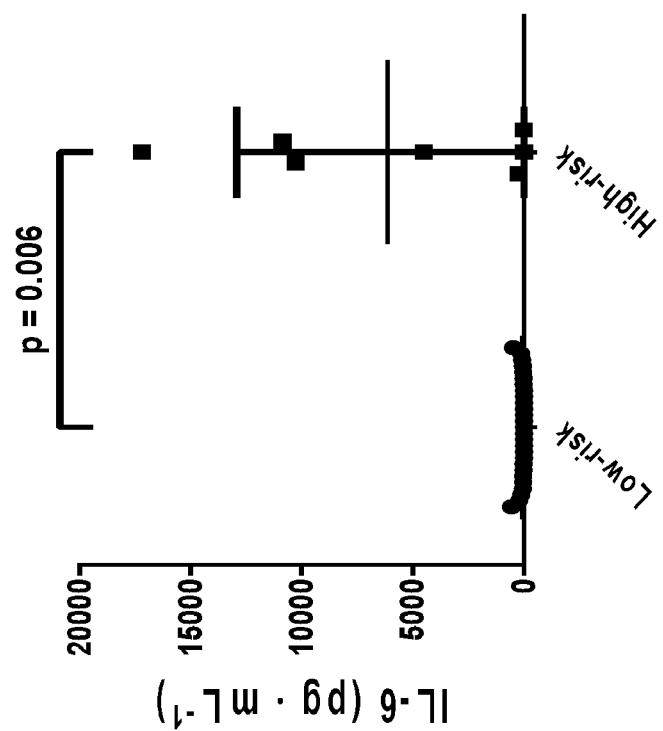
FIG. 17 shows detection of cytokines using devices of embodiments of the present disclosure.
Figure 17:
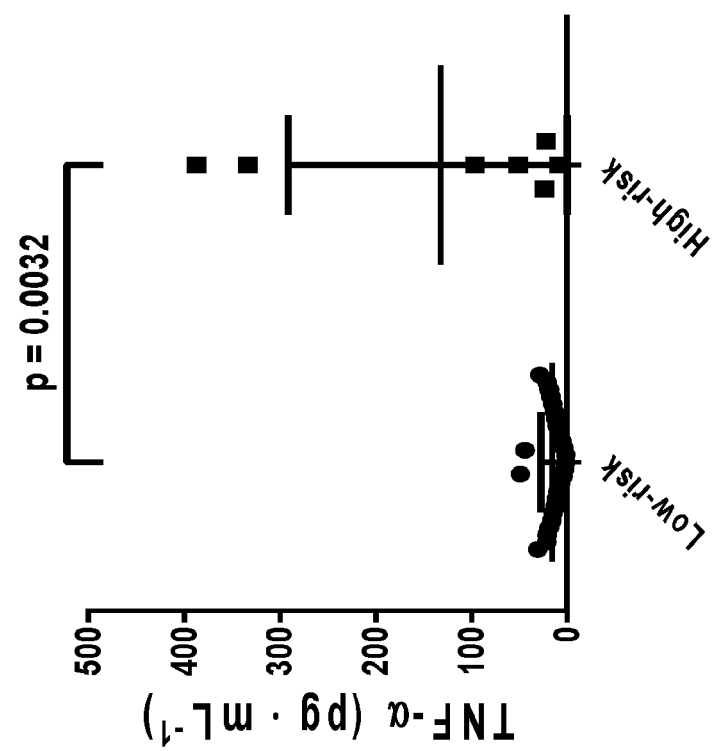

Results: Five serum biomarkers, which together have a negative predictive value for 28-day mortality of 97%, when measured within the first 24 hours of PICU admission, were measured. This panel allows risk stratification of pediatric sepsis patients into low-risk of mortality (<3% probability) and high-risk of mortality (>25% probability) groups, with nearly ⅔ of patients being classified as 'low-risk'. Results (FIG. 17) showed a significant increase of two serum cytokines, tumor necrosis factor alpha (TNF-α) and interleukin-6 (IL-6) in patients identified as high-risk compared to those identified as low-risk (FIG. 17).

Conclusion: The large variability of serum cytokine values within the high-risk group supports the need for rapid cytokine determination to guide precision-targeted anti-cytokine therapy in only those patients with elevated cytokines.

Example 5

This Example describes additional methods of fabricating surfaces.

Chemical vapor deposition of aminated silanes on substrate surface to facilitate AuNR deposition.

Aminated silanes (eg., (3-Aminopropyl)triethoxysilane, (3-Aminopropyl)dimethylmethoxysilane, or (3-Aminopropyl)dimethylethoxysilane) were deposited onto the substrate surface (glass, or thermoplastic polymer (e.g., COP, COC, PMMA) by chemical vapor deposition (CVD) (vacuum, 15-20 in Hg for 18-24 hours). Following CVD AuNRs were patterned on the amine functionalized substrate using a microfluidic patterning technique through dative bonding between the AuNR and the amine functionalized substrate. The constructed AuNR barcode patterns were functioned with thiolated alkane 10-Carboxy-1-decanethiol (HS-$(CH_2)_{10}$-COOH) through ligand exchange and subsequently activated using standard EDC/NHS coupling chemistry. The probe cytokine antibodies were then loaded into individual patterning channels forming a barcode array consisting of six parallel stripes each functioned with distinct antibodies to afford multiplexed detection of 6 different cytokines at one time.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A localized surface plasmon resonance (LSPR) device, comprising:
   a first substrate having a first broad surface;
   an array of metals particles coupled to the first broad surface of the first substrate, wherein the array of metal particles comprises nanoparticles patterned along a first direction relative to the first substrate, and wherein the array of metal particles is functionalized with antibodies specific for at least one polypeptide;
   a second substrate coupled to the first broad surface of the first substrate and defining a plurality of microfluidic channels in fluid communication with the array of metal particles, wherein the plurality of microfluidic channels has an inlet and an outlet and is oriented orthogonal to the first direction, wherein each of the plurality of microfluidic channels has a volume of 10 μl to 10 μL, and wherein a microfluidic channel of the plurality of microfluidic channels comprises a first channel dimension at one of the inlet and the outlet that is smaller than a second channel dimension at an intermediate portion of the microfluidic channel, thereby transmitting the sample, in the assessment mode, by capillary force;
   wherein the device is operable in an assessment mode wherein:
      the plurality of microfluidic channels contains a sample, comprising a target polypeptide component associated with inflammatory response, from a subject,
      an interaction between the target polypeptide component and the antibodies functionalized at the array of metal particles produces a set of signals associated with light scattering, and
      the set of signals is detected at an optical detection platform through at least one of the first substrate and the second substrate.

2. The device of claim 1, wherein said antibodies comprise a plurality of antibodies, wherein each antibody is specific for a different polypeptide.

3. The device of claim 2, wherein the plurality of polypeptides comprises at least one of: cytokines, proteins, antibodies, and nucleic acids.

4. The device of claim 3, wherein the plurality of polypeptides comprise cytokines comprising at least two of interleukin-2 (IL-2); interleukin-4 (IL-4); interleukin-6 (IL-6); interleukin-8 (IL-8); interleukin-10 (IL-10); interleukin-12 (IL-12); interferon-gamma (IFN-y); and tumornecrosis-factor alpha (TNF-a).

5. The device of claim 1, wherein said substrate comprises at least 100 antibodies coupled to the array of metal particles, and wherein the first substrate is treated with at least one of oxygen plasma, UV/ozone, and silanization.

6. The device of claim 1, wherein the first substrate is composed of at least one of glass and thermoplastic.

7. The device of claim 1, wherein the array of metal particles comprises particles composed of at least one of gold, silver, copper, titanium, and chromium fabricated into at least one of: nanorods, nanostars, nanopyramids, nanodiamonds, nanorings, and core-shells.

8. The device of claim 7, wherein said antibodies are attached to surface via a linker, and wherein the linker comprises a is C1-C10 bifunctional thiollinker.

9. The device of claim 1, wherein the first substrate further comprises a plurality of microelectrodes configured for electroosmosis and in operable communication with the array of metal particles.

10. The device of claim 9, wherein metal nanoparticles of the array of metal nanoparticles are in operable communication with pairs of the plurality of microelectrodes, and wherein each of the plurality of microelectrodes is configured to deliver alternating current.

11. The device of claim 1, further comprising:
    a LSPR detection apparatus comprising the optical detection platform, wherein the optical detection platform includes a lens coupled to a motorized stage supporting the first substrate, the lens operable to transmit light from the interaction through a signal filter and to a sensor subsystem in communication with a computing subsystem for processing of the set of signals.

* * * * *